United States Patent [19]

Roger et al.

[11] Patent Number: 4,980,349

[45] Date of Patent: Dec. 25, 1990

[54] SULPHONAMIDES DERIVED FROM DIARYLMETHANES, THE PROCESSES FOR PREPARING THEM AND PHARMACEUTICAL COMPOSITIONS CONTAINING THEM

[75] Inventors: Pierre Roger, Montigny-les Bretonneux; Jean-Paul Fournier, Versailles; Alain Martin, Montrouge; Jean Choay, Paris, all of France

[73] Assignee: SANOFI, Paris, France

[21] Appl. No.: 143,170

[22] PCT Filed: Mar. 12, 1987

[86] PCT No.: PCT/FR87/00070

§ 371 Date: Nov. 12, 1987

§ 102(e) Date: Nov. 12, 1987

[87] PCT Pub. No.: WO87/05601

PCT Pub. Date: Sep. 24, 1987

[30] Foreign Application Priority Data

Mar. 12, 1986 [FR] France ............... 86 03537

[51] Int. Cl.$^5$ .......................... A61K 31/535
[52] U.S. Cl. ............... 574/231.8; 514/232.2;
514/235.8; 514/236.2; 514/236.8; 514/237.2;
514/238.2; 514/316; 514/326; 514/381;
514/382; 514/397; 514/400; 514/401; 514/402;
514/422; 514/428; 514/438; 514/444; 514/445;
514/448; 514/475; 514/521; 514/513; 514/539;
514/559; 514/562; 514/602; 514/603; 544/85;
544/124; 544/130; 544/131; 544/139; 544/141;
544/146; 544/147; 544/159; 546/187; 546/190;
546/191; 546/207; 546/208; 546/210; 546/213;
546/230; 546/232; 546/233; 546/234; 546/235;
548/252; 548/253; 548/336; 548/342; 548/348;
548/350; 548/353; 548/517; 548/518; 548/527;
548/566; 548/568; 549/60; 549/61; 549/64;
549/65; 549/72; 549/75; 549/77; 549/551;
549/553; 558/390; 260/401; 260/402; 560/12;
560/13; 562/430; 564/82; 564/83
[58] Field of Search .............. 260/401, 402; 562/430;
560/12, 13; 549/72, 75, 76, 60, 61, 64, 65, 77,
55, 553; 548/252, 253, 336, 342, 348, 350, 353,
517, 518, 527, 566, 568; 544/112, 113, 121, 120,
122, 124, 85, 130, 131, 139, 141, 146, 147, 159;
546/187, 190, 191, 207, 208, 210, 213, 230, 232,
233, 234, 235; 558/390; 564/82, 83; 574/231.8,
316, 326, 381, 382, 397, 400, 401, 402, 422, 428,
438, 444, 445, 448, 475, 521, 523, 539, 559, 562,
602, 603, 232.2, 235.8, 236.2, 236.8, 237.2, 238.2

[56] References Cited

U.S. PATENT DOCUMENTS 3,666,779  5/1972  Diery et al. ............... 260/401
3,903,114  9/1975  LeMartret et al. ........... 549/72
4,113,463  9/1978  Oshio et al. ................ 532/430
4,198,519  4/1980  Gordie ..................... 549/72
4,443,477  4/1984  Witte et al. ............... 562/430

4,613,618  9/1986  Choay et al. ............... 562/430

FOREIGN PATENT DOCUMENTS 634170   1/1962   Canada ................. 549/72
0064445  11/1982  European Pat. Off. .
0068968  1/1983   European Pat. Off. .
48-72154 9/1973   Japan .................. 260/401
1447054  8/1976   United Kingdom .

Primary Examiner—Bruce Gray
Attorney, Agent, or Firm—Foley & Lardner, Schwartz, Jeffery, Schwaab, Mack, Blumenthal & Evans

[57] ABSTRACT

The invention relates to new compounds corresponding to formula I:

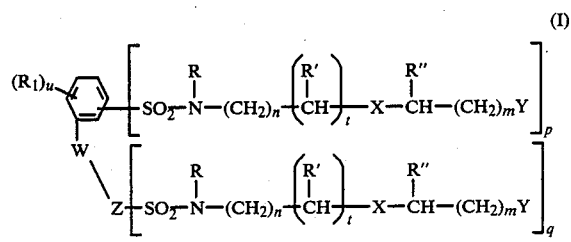

in which:
W represents C=O, CH$_2$ or CHOH,
Z represents

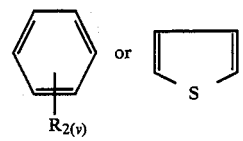

R$_1$ and R$_2$ represent especially Cl or F,
R, R' and R'' represent especially H,
X represents especially CH$_2$,
Y represents especially COOH,
u and v are two integers ranging from 0 to 10,
p and q take the value 0 or 1,
n and m are two integers ranging 0 to 10 and
t is 0 or 1
the total number of carbon atoms in the chain

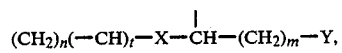

ranging from 2 to 20,
and to their physiologically acceptable salts obtained with organic or inorganic acids.

These compounds are useful for preparing medicinal products which have, especially, anti-inflammatory properties.

42 Claims, No Drawings

SULPHONAMIDES DERIVED FROM DIARYLMETHANES, THE PROCESSES FOR PREPARING THEM AND PHARMACEUTICAL COMPOSITIONS CONTAINING THEM

The invention relates to new compounds, sulphonamides derived from diarylmethanes, in particular benzophenones, and from their isosteres, and also to their corresponding salts.

The invention also relates to a process for preparing these compounds.

The invention also relates to new medicinal products containing, by way of active principle, these new compounds, and also their salts with physiologically acceptable organic or inorganic acids or bases.

By medicinal products there is denoted any pharmaceutical composition containing at least one of the chemical compounds defined below, in combination with a pharmaceutically acceptable vehicle.

Il will be called that the anti-inflammatories which are known and used at present act:

either by inhibiting the biosynthesis of arachidonic acid at the phospholipase $A_2$ level; these are the corticoid anti-inflammatories (cortisones and derivatives), the use of which is limited by their side effects;

or by inhibiting the biosynthesis of prostaglandins at the cyclooxygenase level (both the thromboxane synthetase pathway and also the prostacyclin in synthetase pathway); these are the non-steroid anti-inflammatories.

Among non-steroid anti-inflammatories, there may be mentioned salicyl derivatives such as aspirin, pyrazole derivatives such as phenylbutazone, arylalkanoic acids such as profens, and indole derivatives such as indomethacin.

As regards the non-steroid anti-inflammatories, these act in the biosynthesis of prostaglandins by blocking cyclooxygenase, thereby blocking the formation of thromboxanes and prostacyclins; in particular, they can give rise to haemorrhagic accidents when they are combined with anticoagulant treatments.

The non-steroid anti-inflammatories can cause other adverse side effects, in particular gastralgia, nausea or vomiting, and for this reason they cannot be used in the case of gastric or duodenal ulcer.

In fact, in the phenomena of inflammation, another class of mediators, the leukotrienes, which are metabolites of arachidonic acid, are involved.

The leukotrienes are powerful mediators which are involved in many inflammatory, cardiovascular, allergic, cutaneous or asthmatic conditions.

The subject of the invention is to propose new compounds which are capable of participating in the preparation of medicinal products possessing, in particular, anti-inflammatory properties.

An advantageous aspect of the invention is to propose new compounds which do not inhibit cyclooxygenase and which are involved only at a subsequent stage in the biosynthesis of prostaglandins, endowing them with a more specific action.

One of the aspects of the invention is to propose new compounds which participate in the preparation of medicinal products capable of treating inflammatory phenomena in particular, without affecting the biosynthesis of all prostaglandins.

In effect, they have little or no action on prostacyclin synthetase and do not particularly inhibit the biosynthesis of prostacyclin in ($PGI_2$), which is vasodilatory and inhibits platelet aggregation.

In contrast, and advantageously, they are inhibitors or thromboxane synthetase, an enzyme which is involved in the biosynthesis of thromboxanes. It is known that thromboxane $B_2$, in particular, is involved in the phenomena of vasoconstriction of vessels and of platelet aggregation.

The products of the invention hence have a more specific activity at the platelet level and are devoid of gastric side effects.

An advantageous aspect of the invention is to propose new compounds which have an effect on the biosynthesis of leukotrienes, especially inhibiting 5-lipoxygenase.

One of the aspects of the invention is to propose new compounds which inhibit the biosynthesis of leukotrienes, more especially the leukotrienes $B_4$ ($LTB_4$) which are involved in the inflammatory processes and are produced by the polymorphonuclear luekocytes, and also the leukotrienes $C_4$($LTC_4$) involved in allergic reactions, in particular asthma, and certain types of allergic diseases.

Another aspect of the invention is to propose new compounds which participate in the preparation of medicinal products capable of treating the pathological conditions in which leukotrienes, in particular $LTB_4$ and $LTC_4$, are involved, such as allergic conditions, in particular cutaneous and asthmatic conditions, or inflammatory states.

They can even be administered in the case of renal insufficiency, because they have no inhibitory effect on the vasodilator renal prostaglandins such as $PGE_2$ and $PGF_2$ alpha.

These new compounds can also be used for the preparation of medicaments, liable to treat cardiovascular disorders in which the thromboxane synthetases are implied, for instance prevention of thrombotic accidents.

In particular, the invention proposes new compounds which participate in the formation of medicinal products having effective anti-inflammatory properties and having an improved therapeutic index.

One of the aspects of the invention is to provide a new family of anti-inflammatory medicinal products which can inhibit the biosynthesis of leukotrienes, and have a selective action on thromboxane synthetase.

The invention relates to new sulphonamides derived from diarylmethanes and their isosteres corresponding to formula I:

$$(R_1)_u \left\langle \bigcirc \right\rangle \left[ SO_2-N-(CH_2)_n-\left(CH\right)_t-X-CH-(CH_2)_mY \right]_p \\ \overset{W}{\diagdown} \\ Z \left[ SO_2-N-(CH_2)_n-\left(CH\right)_t-X-CH-(CH_2)_mY \right]_q$$

(I)

with R, R', R'' substituents on N, CH, CH respectively.

in which:

W represents $C=O$, $CH_2$ or $CHOH$,

Z represents;

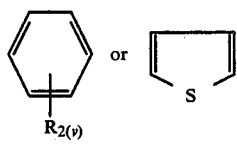

$R_1$ represents Cl, F, Br, $NO_2$, $NH_2$, $CF_3$, an alkyl radical containing 1 to 4 carbon atoms, especially methyl or ethyl, an alkoxy radical containing 1 to 4 carbon atoms, acetamido or benzamido, $R_2$ represents Cl, F, Br, $NO_2$, $NH_2$, $CF_3$, an alkyl radical containing 1 to 4 carbon atoms, especially methyl or ethyl, an lakoxy radical containing 1 to 4 carbon atoms, acetamido or benzamido, R represents H, an alkyl radical containing 1 to 6 carbon atoms or a benzyl radical, R' and R" represent H or an alkyl radical containing 1 to 4 carbon atoms, X represents $(CH_2)_r$, r taking the value 0 or 1, or —CH=CH,

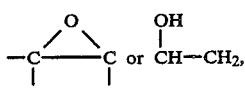

Y represents $COOR_3$, $R_3$ representing hydrogen or an alkyl radical containing 1 to 4 carbon atoms,

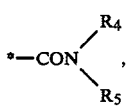

$R_4$ and $R_5$ representing H or an alkyl radical containing 1 to 4 carbon atoms,

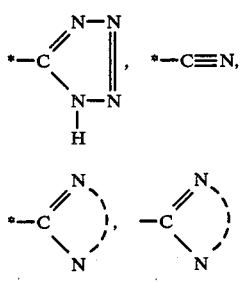

representing a 5- or 6-membered nonaromatic ring, in which the 2 or 3 atoms which form part of the ring are carbon and/or oxygen and/or nitrogen atoms,

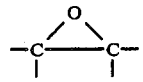

$R_6$ and $R_7$ representing an alkyl radical containing 1 to 4 carbon atoms, or capable of forming, with the nitrogen atom, a nonaromatic cyclic amine such as morpholine, piperidine, or pyrrolidine, on condition that when Y represents $NH_2$, X is other than

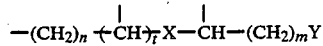

u is an integer from 0 to 2,
v is an integer from 0 to 2,
p takes the value 0 or 1,
q takes the value 0 or 1, p+q being equal to or greater than 1,
n is an integer ranging from 0 to 10,
m is an integer ranging from 0 to 10,
t is 0 or 1,
the total number of carbon atoms in the chain $$-(CH_2)_n-(CH)_t-X-CH-(CH_2)_mY$$

ranging from 2 to 20,
and to their physiologically acceptable salts, obtained with organic or inorganic acids and bases.

The invention also relates to the cis- and trans-isomers of these compounds, when X represents CH=CH, and to the optical isomers, when

or X contains an asymmetric carbon atom, and to the corresponding racemic mixtures and diastereoisomers when

anc X each contain an asymmetric carbon atom.

Along compounds of formula I, a preferred group of compounds consists of those in which W represents C=O.

These compounds correspond to formula II below:

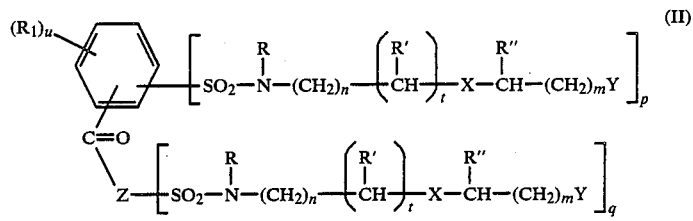

in which $R_1$, R, R', R", X, Y, Z, m, n, p, q, t and u have the meanings given in connection with formula I.

Another advantageous group of compounds of the invention consists of those of formula I in which W represents $CH_2$.

These compounds correspond to formula III below:

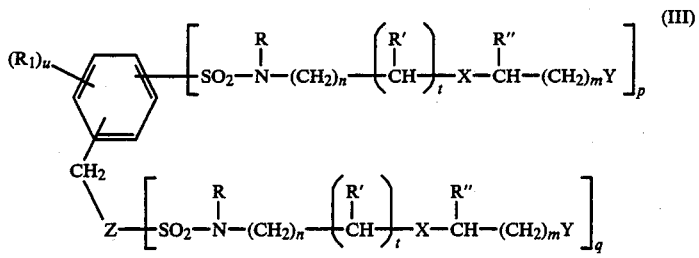

in which $R_1$, R, R', R'', X, Y, Z, m, n, p, q, t and u have the meanings given in connection with formula I.

Another advantageous group of compounds of the invention consists of those of formula I in which W represents CHOH.

These compounds correspond to formula IV below:

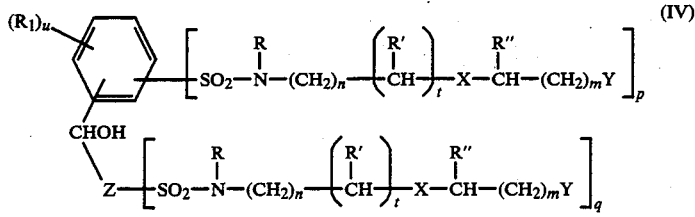

in which $R_1$, R, R', R'', X, Y, Z, m, n, p, q, t and u have the meanings given in connection with formula I.

Among compounds of formula II, an advantageous group of compounds consists of those in which Z represents:

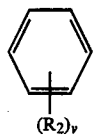

These compounds correspond to formula V below:

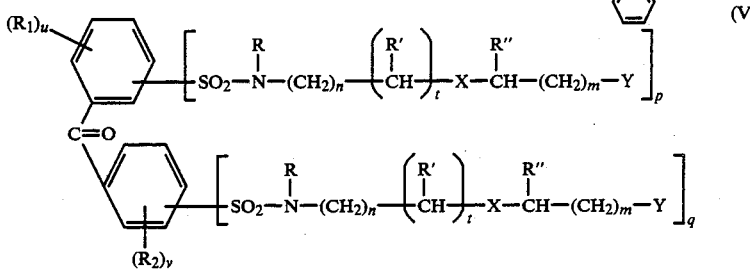

in which $R_1$, $R_2$, R, R', R'', X, Y, m, n, p, q, t, u and v have the meanings given in connection with formula I.

Among compounds of formula V, an advantageous group of compounds of the invention consists of those in which —Y represents —COOR$_3$, $R_3$ representing H or an alkyl radical containing 1 to 4 carbon atoms.

Among compounds of formula V, another advantageous group of compounds of the invention consists of those in which Y represents NH$_2$, NHR$_6$, NR$_6$R$_7$, R$_6$ and R$_7$ representing an alkyl radical containing 1 to 4 carbon atoms, or capable of forming, with the nitrogen atom, a nonaromatic cyclic amine such as morpholine, piperidine or pyrrolidine, on condition that when Y represents —NH$_2$, X is other than

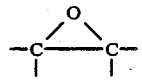

Among compounds of formula V, an advantageous group of compounds of the invention consists of those in which p+q equals 1, i.e. compounds which consist of a single chain; in the case where p=1, these compounds correspond to formula Va below:

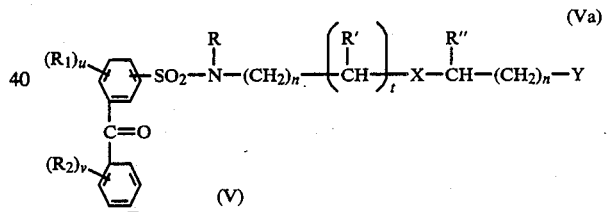

in which $R_1$, $R_2$, R, R', R'', X, Y, n, m, u, t and v have the meanings given in connection with formula I.

Among compounds of formula Va, an advantageous group of compounds of the invention consists of those in which:
  u+v is equal to or greater than 1,
  the total number of carbon atoms in the chain

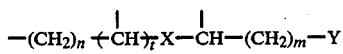

is equal to or greater than 5.

Among compounds of formula V, an advantageous group of compounds of the invention consists of those in which:
p=1,
q=1,
u+v is equal to or greater than 1,
the total number of carbon atoms in the chains

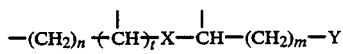

is equal to or greater than 5

These compounds correspond to formula Vb below:

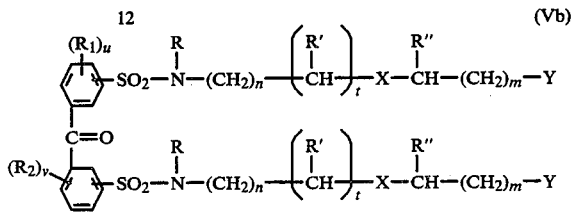

in which $R_1$, $R_2$, R, R', R", X, Y, u, v, n, m and t have the meanings given in connection with formula I.

Among compounds of formula I, an advantageous group of compounds of the invention consists of those in which p+q equals 1, i.e. compounds which consist of a single chain; in the case where p=1, these compounds correspond to formula VI below:

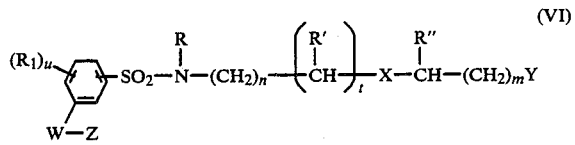

in which $R_1$, R, R', R", X, Y, Z, W, m, n, t and u have the meanings given in connection with formula I.

Among compounds of formula VI, an advantageous group of compounds of the invention consists of those in which the side chain is in the meta-position relative to W.

These compounds correspond to formula VII below:

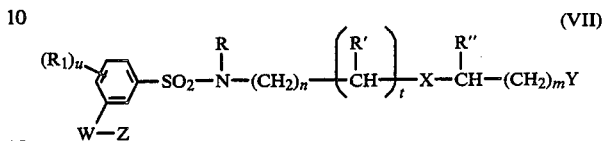

in which $R_1$, R, R', R", X, Y, Z, W, m, n, t and u have the meanings given in connection with formula I.

Among compounds of formula VII, an advantageous group of compounds of the invention consists of those in which Y represents $COOR_3$, $R_3$ representing H or an alkyl radical containing 1 to 4 carbon atoms.

Among compounds of formula VII in which Y represents $COOR_3$, $R_3$ representing H or an alkyl radical containing 1 to 4 carbon atoms, one advantageous group of compounds consists of those in which W represents C=O.

These compounds correspond to formula VIII below:

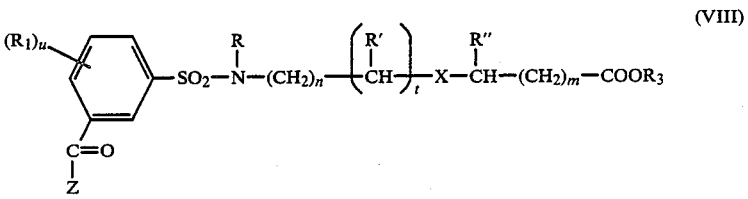

in which $R_1$, $R_3$, R, R', R", X, Z, m, n, t and u have the meanings given in connection with formula I.

Among compounds of formula VII in which Y represents $COOR_3$, $R_3$ representing H or an alkyl radical containing 1 to 4 carbon atoms, an advantageous group of compounds consists of those in which W represents $CH_2$.

These compounds correspond to formula IX below:

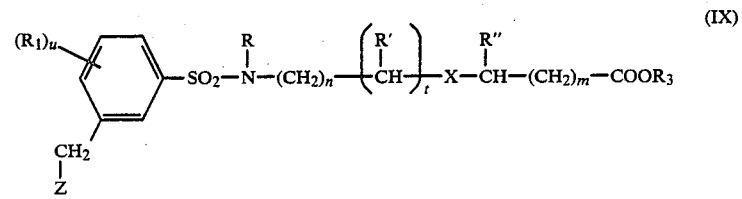

in which $R_1$, $R_3$, R, R', R", X, Z, m, n, t and u have the meanings given in connection with formula I.

Among compounds of formula VII in which Y represents $COOR_3$, $R_3$ representing H or an alkyl radical containing 1 to 4 carbon atoms, an advantageous group of compounds consists of those in which W represents CHOH.

These compounds correspond to formula X below:

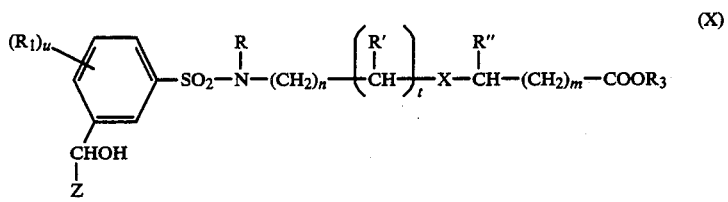

in which $R_1$, $R_3$, $R$, $R'$, $R''$, $X$, $Z$, $m$, $n$, $t$ and $u$ have the meanings given in connection with formula I.

Among compounds of formula VIII, an advantageous group of compounds consists of those in which the total number of carbon atoms in the chain

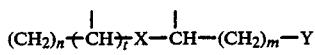

is equal to or greater than 5.

Among compounds of formula IX, an advantageous group of compounds consists of those in which the total number of carbon atoms in the chain

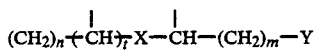

is equal to or greater than 5.

Among compounds of formula X, an advantageous group of compounds consists of those in which the total number of carbon atoms in the chain

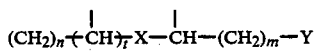

is equal to or greater than 5.

Among compounds of formula VII in which Y represents $COOR_3$, $R_3$ representing H or an alkyl radical containing 1 to 4 carbon atoms, another advantageous group of compounds consists of those in which:

Z represents

the total number of carbon atoms in the chain

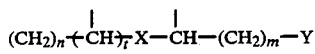

is equal to or greater than 5.

These compounds correspond to formula XI below:

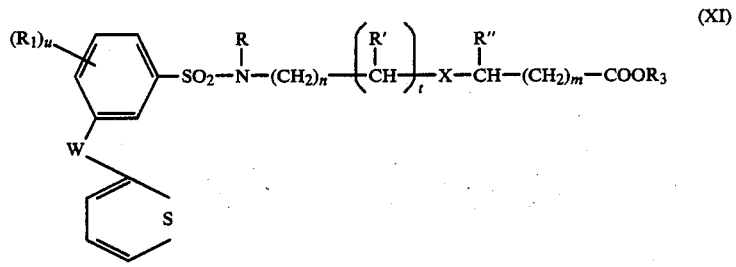

in which $R_1$, $R_3$, $R$, $R'$, $R''$, $X$, $W$, $m$, $n$, $t$ and $u$ have the meanings given in connection with formula I.

Among the compounds of formula VI, an advantageous group of compounds of the invention consists of those of formula VIbis:

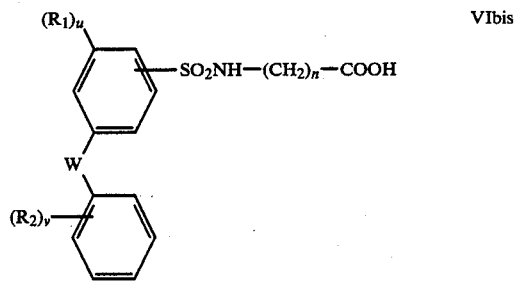

in which $R_1$ and $R_2$ represent a halogen, u and v vary from 0 to 2, W represents C=O, CHOH or $CH_2$ and n varies from 3 to 11.

Among the compounds of formula VI, an advantageous group of compounds consists of those of the following formula VIter:

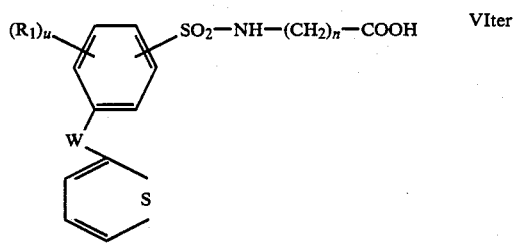

in which $R_1$ represents a halogen, u varies from 0 to 2, W represents C=O, CHOH or $CH_2$ and n varies from 3 to 11.

Particularly advantageous compounds of the invention correspond to the following formulae:

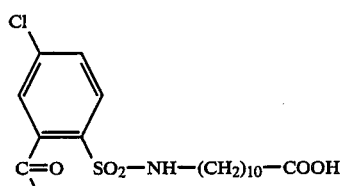
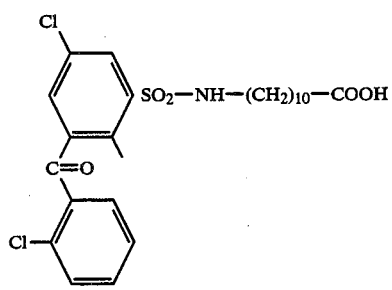
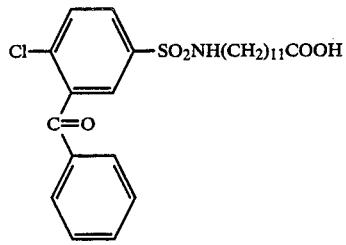
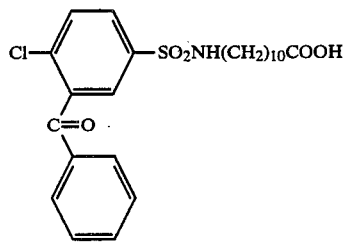
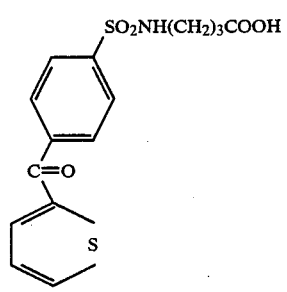
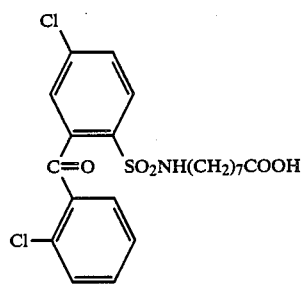
-continued
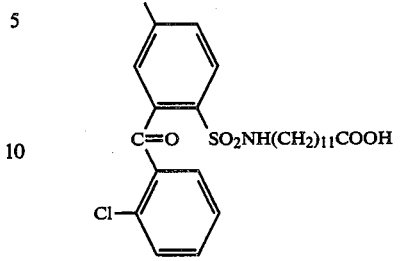
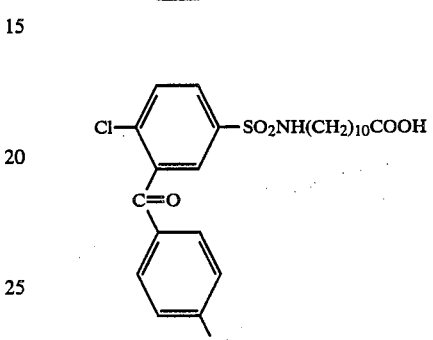
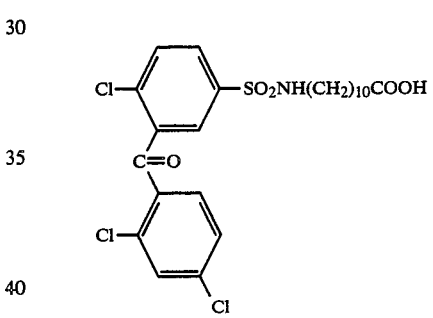
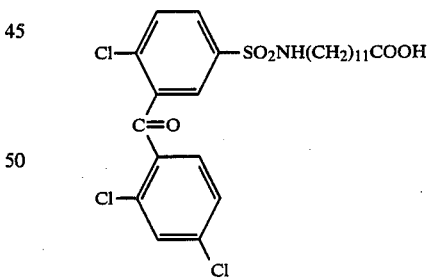
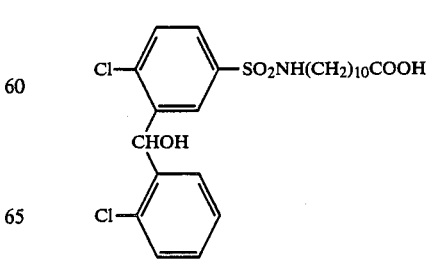

-continued

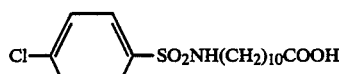
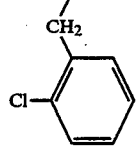

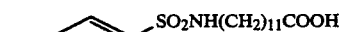
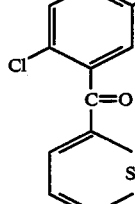

PREPARATION OF THE COMPOUNDS OF THE INVENTION

The compounds of the invention corresponding to formula I:

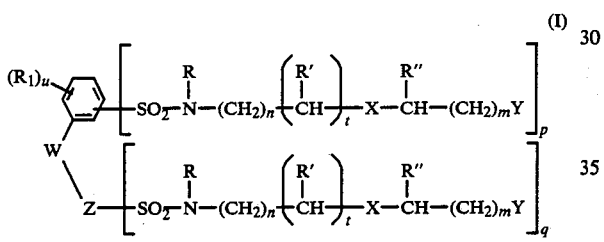
(I)

in which W, Z, $R_1$, R, R', R", X, Y, m, n, p, t and q have the meanings given above, may be prepared:

by subjecting a compound of formula:

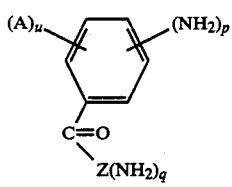

in which:

A has the meanings given for $R_1$, except $NH_2$, i.e. A represents Cl, F, Br, $NO_2$, $CF_3$, an alkyl radical containing 1 to 4 carbon atoms, especially methyl or ethyl, an alkoxy radical containing from 1 to 4 carbon atoms, acetamido or benzamido, and preferably Cl or $NO_2$, Z represents

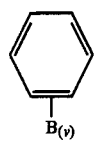 or 

B has the meanings given in the case of $R_2$, except $NH_2$, i.e. B represents Cl, F, Br, $NO_2$, $CF_3$, an alkyl radical containing 1 to 4 carbon atoms, especially methyl or ethyl, an alkoxy radical containing 1 to 4 carbon atoms, acetamido or benzamido, and preferably Cl or $NO_2$, u, v, p and q have the meanings given above, to a reduction, if required, especially using aluminium chloride and lithium aluminium hydride in order to reduce —C=O to $CH_2$, and obtain the compound of formula:

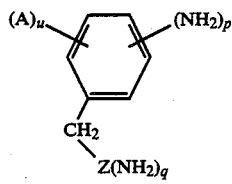

in which A, Z, u, p and q have the meanings given above, by then subjecting the amino compound of formula given above to Sandmeyer reaction (formation of the diazonium salt and action of sulphur dioxide), to obtain a sulphohalide, especially sulphochloride of formula:

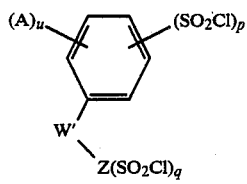

in which A, Z, u, p and q have the meanings given above and W' represents C=O or $CH_2$, by then reacting the sulphohalide, especially the sulphochloride, of formula given above, with one compound of formula:

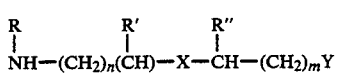

in which:

R represents H, an alkyl radical containing 1 to 6 carbon atoms or a benzyl radical, R' and R" represent H or an alkyl radical containing 1 to 4 carbon atoms, X represents $(CH_2)_r$, r taking the value of 0 or 1, —CH=CH—,

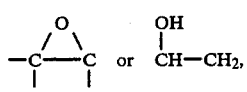

Y represents $COOR_3$, $R_3$ representing H or an alkyl radical containing 1 to 4 carbon atoms,

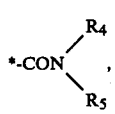

$R_4$ and $R_5$ representing H or an alkyl radical containing 1 to 4 carbon atoms,

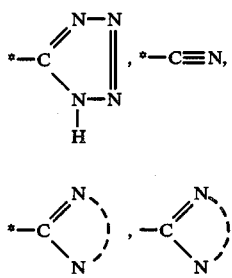

representing a 5- or 6-membered nonaromatic ring, in which the 2 or 3 atoms which form part of the ring are carbon and/or oxygen and/or nitrogen atoms,

* $NH_2$, $NHR_6$, $NR_6R_7$, $R_6$ and $R_7$ representing an alkyl radical containing 1 to 4 carbon atoms or capable of forming, with the nitrogen atom, a nonaromatic cyclic amine such as morpholine, piperidine or pyrrolidine, on condition that when Y represents $NH_2$, X is other than

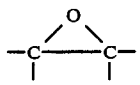

n is an integer ranging from 0 to 10,
m is an integer ranging from 0 to 10,
t is 0 or 1,
the total number of atoms in the chain

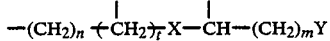

ranging from 2 to 20, in order to obtain the compound of formula:

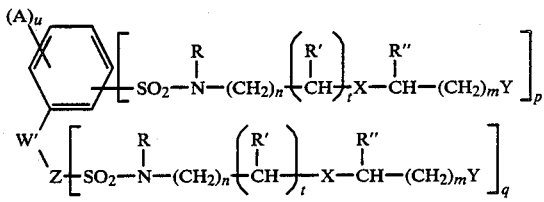

and in the case where W' represents C=O, by subjecting, if required, the above compound to a reduction, expecially using an alkali metal borohydride, such as sodium borohydride, in order to reduce C=O to CHOH, by then carrying out a reduction, if required, when A and/or B represent(s) $NO_2$.

Compounds of the invention of formula II:

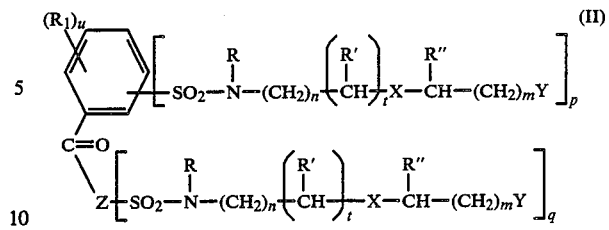

in which $R_1$, R, R', R", X, Y, Z, m, n, p, q, t and u have the meanings given above, mays be prepared by reacting a sulphohalide, especially a sulphochloride of formula:

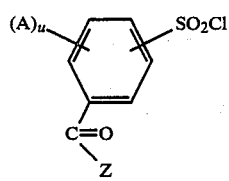

in which A, Z and u have the meanings given above or a disulphohalide, especially a disulphochloride of formula:

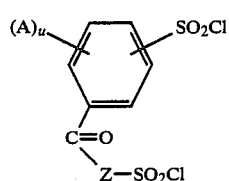

in which A, u and Z have the meanings given above, with one or two compounds of formula:

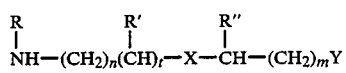

in which R, R', R", n, m, t, X and Y have the meanings given above, followed, if required, by a reduction when A and/or B represent(s) $NO_2$.

Compounds of the invention of formula II may be prepared:

by esterifying a compound as obtained above, and in which Y represents COOH, into a compound of formula II in which Y represents $COR_3$, $R_3$ representing an alkyl radical containing 1 to 4 carbon atoms, or by carrying out a reaction suitable for converting a compound as obtained above and in which Y represents COOH into a compound of formula II in which Y represents:

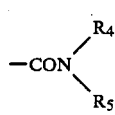

$R_4$ and $R_5$ representing H or an alkyl radical containing 1 to 4 carbon atoms,

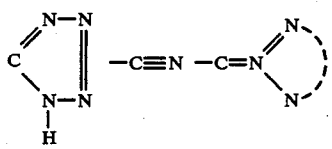

The preparation of the compounds of the invention in which Y represents:

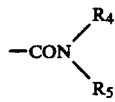

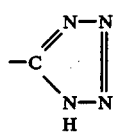

—C≡N

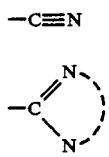

$R_4$ and $R_5$ representing an alkyl group containing 1 to 4 carbon atoms,

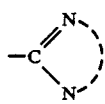

representing a 5- or 6-membered nonaromatic ring in which the 2 or 3 atoms which form part of the ring are carbon and/or oxygen and/or nitrogen atoms, is carried out using compounds in which Y represents COOH, according to conventional methods, for example, as mentioned below:

The conversion of an acid

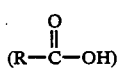

to an amide may be carried out especially according to two methods:

The first of these methods consists:

1) in preparing an acid chloride intermediate according to the reaction scheme below:

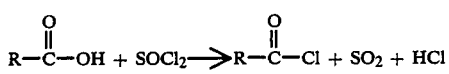

2) and then in reacting an amine with the acid chloride, in the presence of an acceptor for hydrochloric acid, for example a tertiary amine according to the reaction scheme below:

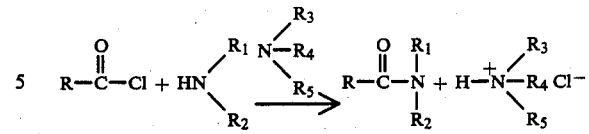

In the first stage, $PCl_3$ or $PCl_5$ may also be used instead of $SOCl_2$.

The second method consists:

1) in preparing an ester intermediate according to the reaction scheme below:

$H^+$ advantageously originating from HCl or HBr, and 2) in reacting an amine, preferably under pressure and at a high temperature, according to the reaction scheme below:

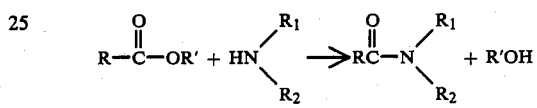

These two methods may be used for the preparation of primary, secondary and tertiary amides, depending on the amine used at the start.

The conversion of an amide group to a nitrile group may be carried out according to two methods.

The first of these methods consists in reacting a dehydrating geagent (phosphorus oxychloride $POCl_3$, phosphorus pentoxide $P_2O_5$ or thionyl chloride $SOCl_2$) with an amide

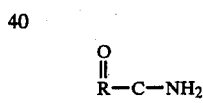

according to the reaction scheme below:

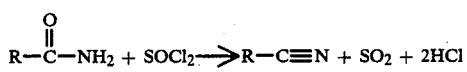

The second method consists in carrying out a pyrolysis of the amide at high temperature, for example at approximately 200° C.:

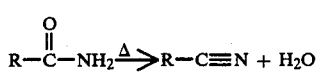

In this case, R may represent either the sulphonamide derived from diarylmethane of formula I, in which Y represents $CONH_2$ or the aminated chain, subsequently condensed with the sulphochloride in order to avoid degradations.

The conversion of the nitrile group to a tetrazole group may be carried out by the cyclocondensation of nitrile with sodium azide according to the reaction scheme below:

$$R-C\equiv N + NaN_3 \xrightarrow{\Delta} R-C\underset{\underset{H}{N}}{\overset{N=N}{\overline{\phantom{XX}}}}N$$

The conversion of an amide into a cyclic compound such as dihydroimidazole or tetrahydropyrimidine may be carried out by a second method which consists in preparing a thioamide intermediate according to the reaction scheme below:

$$R-\overset{O}{\overset{\|}{C}}-NH_2 \xrightarrow[DMF]{P_4S_{10}} R-\overset{S}{\overset{\|}{C}}-NH_2$$

(In this case, R may represent either the sulphonamide derived rom diarylmethane of formula I, in which Y represents CONH$_2$, or the aminated chain, subsequently condensed with the sulpochloride in order to avoid degradations), and then in preparing an isothiouronium compound according to the reaction scheme below:

$$R-\overset{S}{\overset{\|}{C}}-NH_2 \xrightarrow{CH_3I} RC\underset{NH,\ HI}{\overset{SCH_3}{\diagup}}$$

and then in cyclinzing with a diamine according to the reaction scheme below:

$$R-C\underset{NH,\ HI}{\overset{SCH_3}{\diagup}} + \underset{H_2N-}{\overset{H_2N-}{\phantom{X}}}\rceil \longrightarrow R-C\underset{N-CH_2}{\overset{NH-CH_2}{\diagup}}$$

The conversion of an acid $$R-\overset{O}{\overset{\|}{C}}-OH$$

to an imidazole ring may be carried out by the direct condensation of ethylenediamine with the acid according to the reaction scheme below:

$$R-\overset{O}{\overset{\|}{C}}-OH + \underset{H_2N-CH_2}{\overset{H_2N-CH_2}{|}} \longrightarrow$$

$$R-C\underset{N-CH_2}{\overset{NH-CH_2}{\diagup}} \xrightarrow{Pt/Al_2O_3} R-C\underset{\underset{H}{N}}{\overset{N}{\diagdown\!/\!\!\diagup}}\rceil$$

Compounds of the invention of formula II, in which Y represents NH$_2$, NHR$_6$ or R$_6$ and R$_7$ representing an alkyl radical containing 1 to 4 carbon atoms, or forms, with nitrogen, a nonaromatic cyclic amine such as morpholine, piperidine or pyrrolidine, may be prepared by reacting a sulphohalide, especially sulpochloride of formula:

[structure: benzene ring with (A)$_u$ substituent, SO$_2$Cl, and C=O group bonded to Z]

in which:
A represents R$_1$, except NH$_2$, i.e. Cl, F, Br, NO$_2$, CF$_3$, an alkyl radical of 1 to 4 carbon atoms, an alkoxy radical containing 1 to 4 carbon atoms, acetamido or benzamido,
Z represents:

[benzene ring with B$_{(v)}$ substituent] or [thiophene ring with S]

B has the meanings given in the case of R$_2$, except NH$_2$, i.e. B represents Cl, Br, F, NO$_2$, CF$_3$, an alkoxy or alkyl radical containing 1 to 4 carbon atoms, acetamido or benzamido and preferably cl o NO$_2$,
u represents an integer from 0 to 2,
v represents an integer from 0 to 2, or a disulphohalide, especially disulphochloride of formula:

[structure: benzene ring with (A)$_u$, SO$_2$Cl, and C=O bonded to Z—SO$_2$Cl]

in which A, u, Z have the meanings given above, with one of formula:

$$\underset{NH-(CH_2)_n(\overset{R'}{\overset{|}{CH}})_t-X-\overset{R''}{\overset{|}{CH}}-(CH_2)_mY}{\overset{R}{\overset{|}{\phantom{X}}}}$$

in which:
R represents H, an alkyl radical containing 1 to 6 carbon atoms or a benzyl radical,
R' and R'' represent H or an alkyl radical containing 1 to 4 carbon atoms,
n represents an integer ranging from 0 to 10,
m represents an integer ranging from 0 to 10,
t is 0 or 1,
X has the meaning above mentioned,
Y having the meaning NH$_2$, NHR$_6$ or NR$_6$R$_7$, as defined above.

The compounds above in which R$_1$ and/or R$_2$ represent(s) NH$_2$ are prepared by the reduction of compounds in which A and/or B represent(s) NO$_2$, by catalytic hydrogenation or by chemical reduction.

The reaction described above relating to sulphochlorides can also be applied to other sulphohalides, especially to sulphobromides.

An advantageous method for the preparation of the compounds of the invention in which Y represents NH$_2$, NHR$_6$ or NR$_6$R$_7$, as defined above, consists in carrying out the reaction as given below, by way of general example.

0.1 mole of a tertiary amine (such as triethylamine, pyridine and the like) is added, with stirring, to 0.1 mole of (aroyl)phenylsulphonyl chloride dissolved in an organic solvent (ethyl ether, methylene chloride, chloroform and the like) which is cooled in an ice bath, and 0.1 mole of aminoalkylamines dissolved in the same organic solvent is added slowly.

After approximately 12 hours of contact, the reaction medium is brought to ambient temperature, while still being stirred, and is filtered; the filtrater is evaporated to dryness and then taken up with water.

The product obtained is:
either in the form of crystals which are washed with water, drained, dried and then recrystallized in a suitable solvent, or in the form of an oil which is either crystallized directly in a solvent or is, after extraction with an organic solvent (especially ether, ethyl acetate, methylene chloride, or chloroform), drying and evaporation, purified by silica column chromatography and then crystallized in a suitable solvent.

$$SO_2N-(CH_2)_n \underset{R}{-}(CH)_t X-\underset{R''}{CH}-(CH_2)_m-Y$$

are prepared as follows:
One equivalent of disulphochloride is used as the starting material and it is condensed with at least two equivalents of suitable amino acid or aminoalkylamine.

One group of sulphochlorides advantageously used in the preparation of the compounds of the invention corresponding to formula II consists of:
2-benzoyl-4-nitrobenzenesulphonyl chloride
2-benzoyl-4-chlorobenzenesulphonyl chloride
4-chloro-2-(2-chlorobenzoyl)benzenesulphonyl chloride
2-benzoylbenzenesulphonyl chloride
2-(4-chlorobenzoyl)benzenesulphonyl chloride
4-benzoylbenzenesulphonyl chloride
3-benzoylbenzenesulphonyl chloride
3-(2,4-dichlorobenzoyl)-4-chlorobenzensulphonyl chloride
3-benzoyl-4-chlorobenzenesulphonyl chloride 3-(4-chlorobenzoyl)-4-chlorobenzenesulphonyl chloride 4-benzoyl-3-chlorobenzenesulphonyl chloride and 4-chloro-3-(2-thienoyl)benzenesulphonyl chloride.

One group of amino acids advantageously used in the preparation of the compounds of the invention of formula II consists of:

$NH_2(CH_2)_n-COOH$
n varying from 1 to 11.

One group of dialkylaminoalkylamines advantageously used in the preparation of compounds of formula II of the invention consists of:

$$NH_2-(CH_2)_n-N\underset{R_7}{\overset{R_6}{\diagdown}} \quad n = 2 \text{ or } 3.$$

$R_6$ and $R_7$ representing an alkyl group of 1 to 4 carbon atoms or forming a morpholine group with the nitrogen atom.

Compounds of the invention of formula III:

$$(R_1)_u\text{-}\underset{}{\bigcirc}\left[-SO_2-\underset{R}{N}-(CH_2)_n\left(\underset{R'}{CH}\right)_t-X-\underset{R''}{CH}-(CH_2)_mY\right]_p \tag{III}$$

$$\underset{CH_2}{\diagdown}Z-\left[-SO_2-\underset{R}{N}-(CH_2)_n\left(\underset{R'}{CH}\right)_t-X-\underset{R''}{CH}-(CH_2)_mY\right]_q$$

in which $R_1$, R, R', R'', X, Y, Z, m, n, p, q, t and u have the meanings given above may be prepared by subjecting the compound of formula:

$$(A)_u\text{-}\underset{}{\bigcirc}\underset{\underset{Z}{C=O}}{\overset{NH_2}{}}$$

or of formula:

$$(A)_u\text{-}\underset{}{\bigcirc}\underset{\underset{Z-NH_2}{C=O}}{\overset{NH_2}{}}$$

to a reduction, especially using aluminium chloride and lithium aluminium hydride, in order to reduce C=O to CH_2 and to obtain the compound of formula:

$$(A)_u\text{-}\underset{CH_2\diagdown Z}{\bigcirc}\text{-}NH_2 \quad \text{or} \quad (A)_u\text{-}\underset{CH_2\diagdown Z-NH_2}{\bigcirc}\text{-}NH_2$$

by subjecting one of these compounds to Sandmeyer reaction (formation of the diazonium salt and action of sulphur dioxide) to obtain compounds of formula:

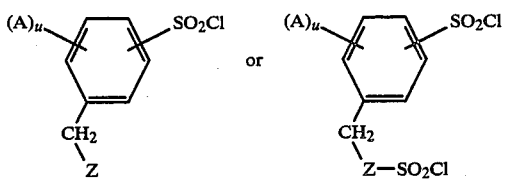

and then by condensing the sulphohalide or the disulphohalide of formula given above, with one compound of formula:

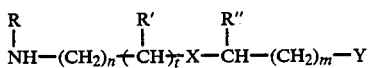

in which R, R', R", X, Y, n, m and t have the meanings given above, followed, if required, by a reduction when A and/or B represent(s) $NO_2$.

One group of amino acids or of dialkylaminoalkylamines advantageously used for the preparation of the compounds of formula III is chosen from amongst:

$NH_2-(CH_2)_n-COOH$  n varying from 1 to 11

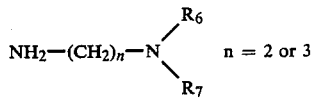  n = 2 or 3

$R_6$ and $R_7$ representing an alkyl group of 1 to 4 carbon atoms or forming a morpholine group with the nitrogen atom.

The compounds of formula:

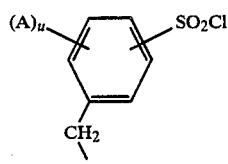

preferred for the preparation of the compounds of formula III are chosen from amongst:

3-(2,4-dichlorobenzyl)-4-chlorobenzenesulphonyl chloride
3-(4-chlorobenzyl)-4-chlorobenzenesulphonyl chloride
2-benzyl-4-chlorobenzenesulphonyl chloride
2-(2,4-dichlorobenzyl)-4-chlorobenzenesulphonyl chloride
2-(4-chlorobenzyl)-4-chlorobenzenesulphonyl chloride
4-benzyl-3-chlorobenzenesulphonyl chloride
4-(2,4-dichlorobenzyl)-3-chlorobenzenesulphonyl chloride
4(4-chlorobenzyl)-3-chlorobenzenesulphonyl chloride and
3-benzyl-4-chlorobenzenesulphonyl chloride.

Compounds of the invention of formula IV:

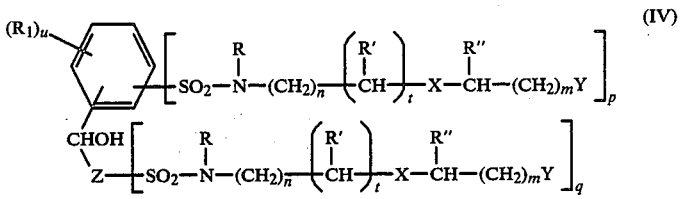

in which $R_1$, R, R', R", X, Y, Z, m, n, p, q, t and u have the meanings given above, may be prepared by subjecting the compound of formula II:

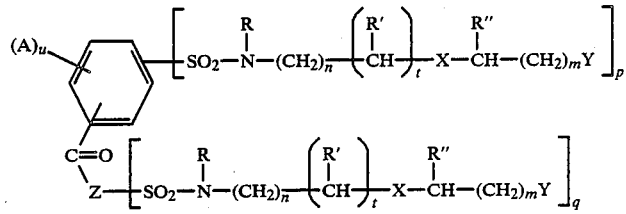

in which A, X, Y, Z, R, R', R", m, n, p, q, t and u have the meanings given above, and obtained as above, before the reduction, when required, of A and/or B when they represent $NO_2$, to a reduction to convert C=O into CHOH, using an alkali metal borohydride, especially sodium borohydride.

One group of amino acids or of dialkylaminoalkylamines advantageously used for the preparation of compounds of formula IV is chosen from amongst:

$NH_2-(CH_2)_n-COOH$  n varying from 1 to 11

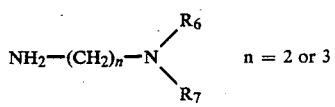  n = 2 or 3

$R_6$ and $R_7$ representing an alkyl group of 1 to 4 carbon atoms or forming a morpholine group with the nitrogen atom.

The sulphochlorides advantageously used for the preparation of the compounds of formula IV are chosen from amongst:
2-benzoyl-4-nitrobenzenesulphonyl chloride
2-benzoyl-4-chlorobenzenesulphonyl chloride
4-chloro-2-(2-chlorobenzoyl)benzenesulphonyl chloride
2-benzoylbenzenesulphonyl chloride
2(4-chlorobenzoyl-benzenesulphonyl chloride
4-benzoylbenzenesulphonyl chloride 3-benzoylbenzenesulphonyl chloride
3(2,4-dichlorobenzoyl)-4-chlorobenzenesulphonyl chloride
3-benzoyl-4-chlorobenzenesulphonyl chloride
3-(4-chlorobenzoyl)-4-chlorobenzenesulphonyl chloride
4-benzoyl-3-chlorobenzenesulphonyl chloride and
4-chloro-3-(2-thenoyl)benzenesulphonyl chloride.

Compounds of the invention corresponding to formula V below:

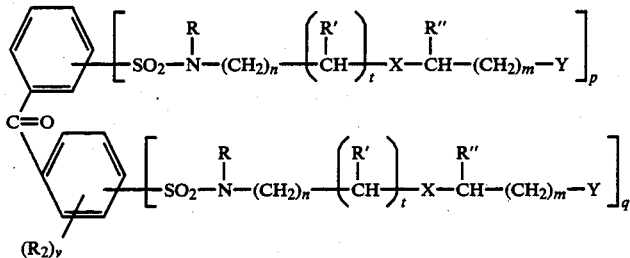

in which $R_1$, $R_2$, R, R', R", X, Y, m, n, p, q, t, u and v have the meanings given above, may be prepared by reacting a sulphohalide, especially a sulphochloride of formula:

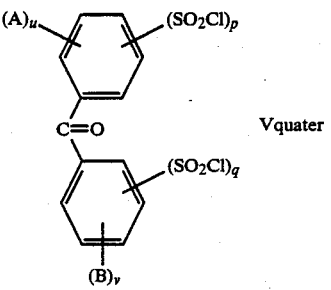

Vquater in which A, B, p, q, u and v have the meanings given above, or a disulphohalide, especially a disulphochloride of formula:

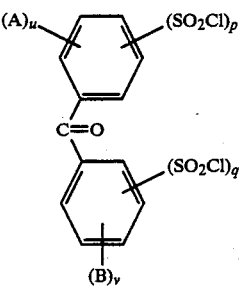

in which A, B, p, q, u and v have the meanings given above with one compound of formula:

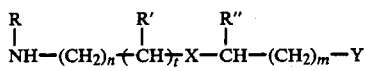

in which R, R', R", m, n, t, X and Y have the meanings given above, followed, if required, by a reduction when A and/or B represent(s) $NO_2$.

Compounds of formula V in which:
Y represents COOH
may be prepared by reacting a sulphochloride of formula Vquater, with one amino acid of formula:

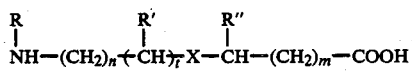

in which R, R', R", n, m, t and X have the meanings given above.

Compounds in which Y represents $COOR_3$ ($R_3$ being different from H), especially $COOC_2H_5$, may be prepared by the esterification of compounds of the invention in which Y represents —COOH.

Compounds of the invention of formula V, in which Y represents $COOR_3$, $R_3$ representing H or an alkyl group containing 1 to 4 carbon atoms, and in which $R_1$ represents $NH_2$ and/or $R_2$ represents $NH_2$, are prepared by reducing compounds in which A represents $NO_2$ and/or B represents $NO_2$, by catalytic hydrogenation or by chemical reduction.

The reaction described above for the sulphochlorides may also be applied to other sulphohalides, especially sulphobromides.

The compounds of the invention, especially those of formula V, in which Y represents $COOR_3$, $R_3$ representing H or an alkyl radical containing 1 to 4 carbon atoms, are advantageously prepared by the following procedure, given by way of general example:

0.2 mole of amino acid dissolved in 4 equivalents of an aqueous basic solution (for example caustic soda, caustic potash or ammonia) is added to 0.1 mole of (aroyl)phenylsulphonyl chloride dissolved in an organic solvent which has a very low solubility in water (for example ethyl ether, methylene chloride or chloroform).

The reaction medium is stirred vigorously until the sulphochloride disappears (as tested by thin layer chromatography or by gas chromatography).

After removing the organic phase, the pH of the aqueous phase is adjusted to approximately 1 to 3 by adding an aqueous 1 N to 10 N, preferably 5 N, acid solution (for example hydrochloric acid or sulphuric acid).

So, the product obtained is:
either in the form of crystals which are drained and then dried before being recrystallized in a suitable solvent,
or in the form of an oil, which is either crystallized directly in a solvent or is, after extracting with an organic solvent (especially ether, ethyl acetate, methylene chloride or chloroform), drying and evaporation, purified by silica column chromatography and then crystallized directly in a suitable solvent.

The compounds of the invention of formula VI:

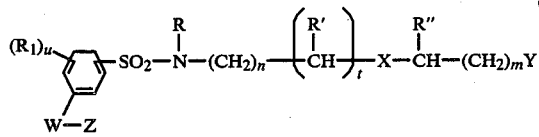
(VI)

in which $R_1$, R, R', R'', X, Y, Z, W, m, n, t and u have the meanings given above may be prepared by subjecting a compound of formula:

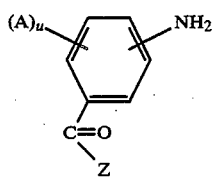

in which A, Z and u have the meanings given above, if required, to a reduction, especially using aluminium chloride and lithium aluminium hydride to reduce $C=O$ to $CH_2$, and to obtain the compound of formula:

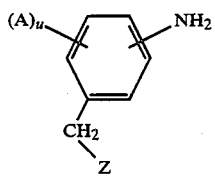

in which A, Z and u have the meanings given above, by then subjecting one of the amino compounds of formula given above to Sandmeyer reaction (formation of the diazonium salt and action of sulphur dioxide), to obtain a sulphohalide of formula:

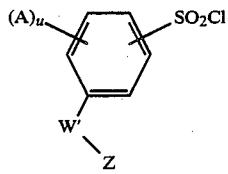

in which A, Z and u have the meanings given above and W' represents $C=O$ or $CH_2$, by reacting the sulphohalide, especially the sulphochloride, of formula given above, with one compound of formula:

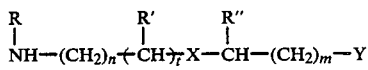

in which R, R', R'', m, n, t, X and Y have the meanings given above, to obtain the compounds of formula:

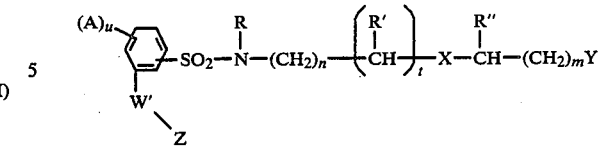

and in the case where W' represents $C=O$, by subjecting, if required, the above compound to a reduction, especially using an alkali metal borohydride such as sodium borohydride, to reduce $C=O$ into CHOH, by then carrying out a reduction, if required, when A and/or B represent(s) $NO_2$.

The compounds of the invention of formula VII:

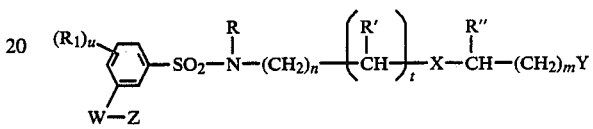

in which $R_1$, R, R', R'', X, Y, Z, W, m, n, t and u have the meanings given above, may be prepared by subjecting a compound of formula:

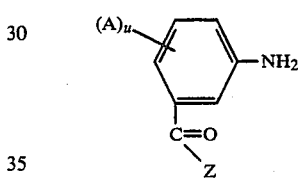

in which A, Z and u have the meanings given above, if required, to a reduction, especially using aluminium chloride and lithium aluminium hydride to reduce $C=O$ to $CH_2$, and to obtain the compound of formula:

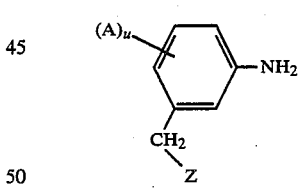

in which A, Z and u have the meanings given above, by then subjecting one of the amino compounds of formula given above to Sandmeyer reaction (formation of the iazonium salt and action of sulphur dioxide), to obtain a sulphohalide of formula:

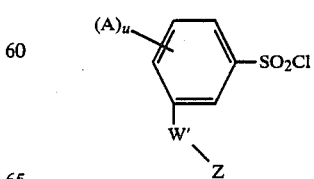

in which A, Z and u have the meanings given above and W' represents $C=O$ or $CH_2$, by reacting the sulphohalide, especially the sulphochloride, of formula given above, with one or two compounds of formula:

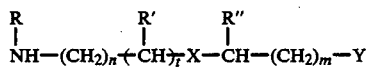

in which R, R', R", X, Y, m, n and t have the meanings given above,
to obtain the compound of formula:

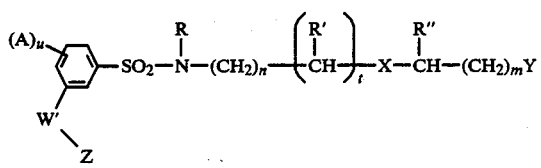

and in the case where W' represents C=O, by subjecting, if required, the above compound to a reduction, especially using an alkali metal borohydride, such as sodium borohydride, to reduce C=O to CHOH,
by then carrying out a reduction, if required, when A and/or B represent(s) $NO_2$.

The compounds of the invention of formula VII, in which:
Y represents $COOR_3$, $R_3$ representing H or an alkyl radical containing 1 to 4 carbon atoms, may be prepared by subjecting a compound of formula:

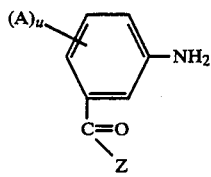

in which A, Z and u have the meanings given above, if required, to a reduction, especially using aluminium chloride and lithium aluminium hydride to reduce C=O to $CH_2$, and to obtain the compound of formula:

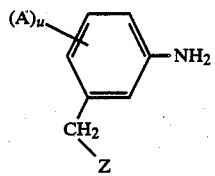

in which A, Z and u have the meanings given above,
by then subjecting one of the amino compounds of formula given above to Sandmeyer reaction (formation of the diazonium salt and action of sulphur dioxide), to obtain a sulphahalide of formula:

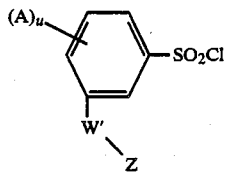

in which A, Z and u have the meanings given above and W' represents C=O or $CH_2$,
by reacting the sulphohalide, especially the sulphochloride, of formula given above, with one or two compounds of formula:

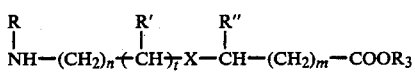

in which R, R', R", X, $R_3$, m, n and t have the meanings given above, to obtain the compound of formula:

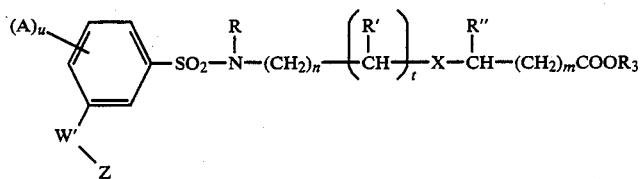

and in the case where W' represents C=O, by subjecting, if required, the above compound to a reduction, especially using an alkali metal borohydride, such as sodium borohydride, to reduce C=O to CHOH,
by then carrying out a reduction, if required, when A and/or B represent(s) $NO_2$.

The compounds of formula VIII, IX and X corresponding to the compounds of formula VII in which Y represents $COOR_3$, $R_3$ representing H or an alkyl group containing 1 to 4 carbon atoms, and in which W represents C=O (compounds of formula VIII), $CH_2$ (compounds of formula IX) and CHOH (compounds of formula X) respectively, are prepared by following the procedure given in the case of compounds of formula VII, in which Y represents $COOR_3$ using appropriate intermediate compounds.

The compounds of the invention of formula XI:

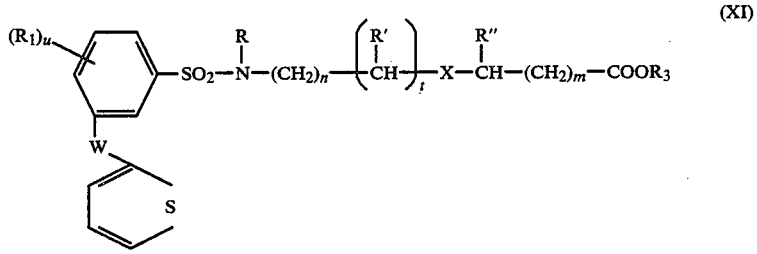

(XI)

in which:
the total number of carbon atoms in the chain

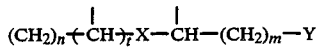

is equal to or greater than 4, and in which:

$R_1$, $R_3$, R, R', R'', X, W, m, n, t and u have the meanings given above, may be prepared by subjecting the compound of formula:

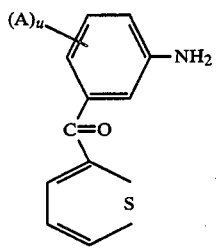

in which:
A and u have the meanings given above, if required, to a reduction, especially using aluminium chloride and lithium aluminium hydride to reduce C=O to CH$_2$, and to obtain the compound of formula:

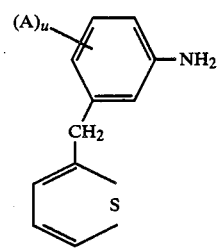

in which A and u have the meanings given above,
by then subjecting the amino compound of formula given above to Sandmeyer reaction (formation of the diazonium salt and action of sulphur dioxide), to obtain a sulphohalide of formula (A)

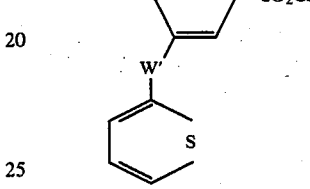

in which A and u have the meanings given above and W' represents C=O or CH$_2$, by the reacting the sulphohalide, especially the sulphochloride, of formula given above, with a compound of formula:

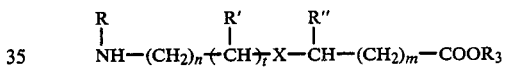

in which R, R', R'', X, m, n, t and $R_3$ have the meanings given above,
to obtain the compound of formula:

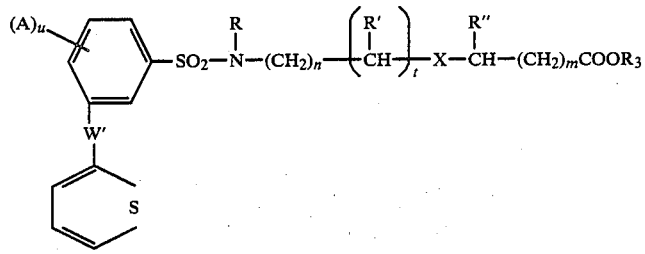

and in the case where W' represents C=O, by subjecting, if required, the above compound to a reduction, especially using an alkali metal borohydride, such as sodium borohydride, to reduce C=O into CHOH, by then carrying out a reduction, if required, when A and/or B represent(s) NO$_2$.

The sulphochlorides used in the preparation of the compounds of the invention may be prepared according to conventional processes.

The sulphochlorides which lead to compounds of the invention in which the side chain is in the orthoposition relative to C=O may be prepared by using optionally substituted 2-nitrobenzophenone, which is reduced by a known method into optionally substituted 2-aminobenzophenone, which is converted into sulphohalide, especially into 2-benzoylbenzenesulphonyl chloride, by a Sandmeyer reaction.

The sulphochlorides which lead to compounds of the invention in which the side chain is in the meta- or in the para- position relative to C=O are prepared by following the procedure given above using appropriate starting products.

The isulphochlorides are prepared starting with the corresponding diamino compounds by a Sandmeyer reaction which consists in:
1) diazotization with nascent nitrous acid ($NaNO_2$, HCl or $NaNO_2$, formic acid or $NaNO_2$, acetic acid),
2) adding the diazonium salt to a saturated solution of sulphur dioxide dissolved in acetic acid in the presence of cupric chloride.

The iamines listed below are prepared according to procedures given in the literature:
2-aminophenyl-3-aminophenylketone
  described in CA 61 7186e
2-aminophenyl-4-aminophenylketone
  described in CA 44 2960g from the corresponding dinitro compound, reduced chemically
  described in CA 61 7186e
3-aminophenyl-3-aminophenylketone
  described in CA 43 3136e, 8061e, CA 61 7186e.

The thenoylbenzenesulphonyl chlorides are prepared according to the technique of G. Holt and B. Padgin, J. Chem. Soc. 1960, 2508, by the Friedel and Crafts reaction:
  either by starting directly with a chlorosulphonylated benzoyl chloride by reacting the thiophene in the presence of aluminium chloride,
  or by starting with a nitrobenzoyl chloride which is reacted with the thiophene in the presence of aluminium chloride, thenitrodiarylketone obtained then being reduced chemically or catalytically into amino diarylketone which, after a Sandmeyer reaction, gives the sulphochloride expected.

The following examples, which relate to the preparation of a number of sulphochlorides and of new compounds of the invention, are given to illustrate the invention, without implied limitation.

EXAMPLE 1

Preparation of 2-benzoyl-4-nitrobenzenesulphonyl chloride 72.6 g (0.3 mole) of 2l-amino-5-nitrobenzophenone are added to a mixture of 225 ml of a solution of hydrochloric acid (d=1.18) and 75 ml of pure acetic acid, in small portions. The reaction medium is stirred and then cooled to approximately -5° C. and maintained at this temperature while adding, drop by drop, a solution of sodium nitrite (21.75 g in 75 ml of water).

When the addition is complete, the reaction medium is stirred at -5° C. for 45 minutes, and then filtered.

The filtrate is added, in portions, to a saturated solution of sulphur dioxide in acetic acid (750 ml) which is cooled to 0° Celsius and contains 16.5 g of cupric chloride.

The mixture, having been vigorously stirred for 3 hours, is poured onto crushed ice. The sulphochloride precipitate is dried, washed several times with water and then dried under vacuum.

The product (62.5 g) is crystallized in a benzene-cyclohexane mixture. It has the empirical formula: $C_{13}H_8ClNO_5S$ (325.71); yield: 65%; m.p. 161° C.

This compound is a new product.

EXAMPLE 2

Preparation of 4-chloro-2-(2-chlorobenzoyl)benzenesulphonyl chloride

The reaction is carried out as described above in Example 1, using 2-amino-5-chlorophenyl-2-chlorophenylketone as the starting product.

The characteristics of the product obtained are as follows:

$C_{13}H_7Cl_3O_3S$ (349.61); yield 58%; m.p. 100° C.

This compound is a new product.

EXAMPLE 3

Preparation of 2-benzoylbenzenesulphonyl chloride

The reaction is carried out as described above in Example 1, using 2-aminobenzophenone as the starting product.

The characteristics of the product obtained are as follows:

$C_{13}H_9ClO_3S$ (280.72); yield 30%; m.p. 99° C.

EXAMPLE 4

Preparation of 2-(4-chlorobenzoyl)benzenesulphonyl chloride

The reaction is carried out as described above in Example 1, using 2-aminophenyl-4-chlorophenylketone as the starting product.

The product obtained has the following characteristics:

$C_{13}H_8Cl_2O_3S$ (315.17); yield 53%; m.p. 70° C.

EXAMPLE 5

Preparation of 4-benzoylbenzenesulphonyl chloride

The reaction is carried out as described above in Example 1, using 4-aminobenzophenone.

The characteristics of the product obtained are as follows:

$C_{13}H_8Cl_4O_3S$ (280.72); yield: 70%; m.p. 90° C.

EXAMPLE 6

Preparation of a compound of the invention in which the side chain is acid 11-(2-benzoyl-4-chlorobenzenesulphonamido)undecanoic acid (compound No. 1572).

24.16 g (0.12 mole) of 11-aminoundecanoic acid in 250 ml of normal caustic soda are added to 37.9 g (0.12 mole) of 2-benzoyl-4-chlorobenzenesulphonyl chloride in 250 ml of methylene chloride, at 0° C. and with stirring.

After stirring for 6 hours at ambient temperature, the organic phase is removed. The pH of the aqueous phase is adjusted to 2 by adding a 2 N hydrochloric acid solution.

After extracting with ethyl acetate, washing the organic phase with water, drying over sodium sulphate and evaporating under reduced pressure, the residue is crystallized in petroleum ether to give 44.5 g of white crystals with a melting point of 70° C.

The reaction yield is 77.2%.

EXAMPLE 7

Preparation of a compound of the invention which contains two acid side chains.

The procedure in Example 6 above is followed, using 2 molecules of amino acid for 1 molecule of sulphochloride.

EXAMPLE 8

Preparation of a compound of the invention in which the side chain is aminated.

(Compound No. 1344): 2-benzoyl-4-chloro-N-(3-morpholinopropyl)benzenesulphonamide.

7.5 ml of redistilled triethylamine are added to 4.72 g (0.015 mole) of 2-benzoyl-4-chlorobenzenesulphonyl chloride in 45 ml of anhydrous methylene chloride, and 2.16 g (0.015 mole) of 3-morpholinopropylamine in 10 ml of anhydrous methylene chloride are then added at 0° C.

After stirring for 3 hours at ambient temperature, the precipitate (triethylamine hydrochloride) is drained.

The filtrate is evaporated to dryness under vacuum and taken up with 20 ml of water.

The crystals obtained are drained, washed with water until the washings are free of chloride ions and then dried before being recrystallized in a cyclohexanebenzene (1:1) mixture.

4.93 g of white crystals with a melting point of 116° C. are obtained. The reaction yield is 80%.

EXAMPLE 9

Preparation of 4-[4(2-thenoyl)benzenesulphonamido]butyric acid a) Preparation of 4-nitrophenyl-2-thienylketone 15 g of aluminium chloride, followed by 10 ml of thiophene (0.18 mole), are carefully added to 11.14 g (0.06 mole) of 4-nitrobenzoyl chloride in 150 ml of methylene chloride. After stirring for 4 hours at ambient temperature, the reaction mixture is poured onto ice.

After extracting with dichloromethane, drying the organic phase over sodium sulphate and evaporating under vacuum, the residue is purified by silica column chromatography using dichloromethane as the eluent.

6.25 g of the nitrated derivative (yellow product), with a melting point of 172° C., are obtained.

b) Preparation of 4-aminophenyl-2-thienylketone

4-Aminophenyl-2-thienylketone is obtained by catalytic reduction of the nitrated compound above at atmospheric pressure using palladinized charcoal (10% palladium) as the catalyst and ethyl acetate as the solvent.

When the theoretical amount of hydrogen is absorbed, the catalyst is removed by filtration, the organic phase is evaporated to dryness, and the residue is taken up with a 2 N hydrochloric acid solution.

The pH of the acid aqueous phase which is washed with ether is then made alkaline. The crystals obtained corresponding to the product expected have a melting point of 120° C.

c) Preparation of 4-(2-thenoyl)benzenesulphonyl chloride

The procedure used is that described above for the Sandmeyer reaction (Example 1).

Starting with 609 mg ($3.10^{-3}$ mole) of 4-aminophenyl-2-thienylketone, 400 mg of 4-(2-thenoyl)benzenesulphonyl chloride are obtained in the form of crystals with a melting point of 118° C.

d) Preparation of 4-[4-(2-thenoyl)benzenesulphonamido]butyric acid 103 mg ($1.10^{-3}$ mole) of 4-aminobutyric acid dissolved in 4 ml of a 0.5 N solution of caustic soda are added dropwise to 287 mg ($1.10^{-3}$ mole) of 4-(2-thenoyl)benzenesulphonyl chloride in 5 ml of ethyl ether.

After stirring for 2 hours at ambient temperature, the organic phase is removed by decantation. The pH of the aqueous phase is adjusted to 2 by adding a 4 N solution of hydrochloric acid.

The crystals are drained, and then washed with the minimum amount of water until the washings are free of $Cl^-$ ions.

After drying under vacuum, the crystals obtained (200 mg) have a meting point of 128°–130° C.

The compounds of Table I below were prepared according to the process described in Example 6.

EXAMPLE 10

Preparation of 3-(2,4-dichlorobenzoyl)-4-chlorobenzenesulphonyl chloride a) Preparation of 2,2',4'-trichloro-5-nitrobenzophenone 6 g of aluminium chloride are added to 5 g of 2-chloro-5-nitrobenzoyl chloride in 60 ml of dichloromethane, and 30 ml of 1,3-dichlorobenzene are then added dropwise. The reaction medium is heated for 2 hours at 80° C. and then cooled, and poured onto crushed ice. After extracting with dichloromethane, washing with water and drying over sodium sulphate, the organic phase is evaporated to dryness under vacuum and the crystalline residue is recrystallized in cyclohexane (3.6 g).

$C_{13}H_6Cl_3NO_3$ (330.55); yield: 48%; m.p. 117° C.

b) Preparation of 5-amino-2,2',4'-trichlorobenzophenone 7.5 g of 2,2',4'-trichloro-5-nitrobenzophenone in 100 ml of ethyl acetate are hydrogenated at atmospheric pressure and at ambient temperature in the presence of palladinized charcoal.

After removing the catalyst, the reaction medium is evaporated to dryness under vacuum and it gives a crystalline residue weighing 6.6 g.

$C_{13}H_8Cl_3NO$ (300.57); yield: 88%; m.p. 103° C.

c) Preparation of 4-chloro-3-(2,4-dichlorobenzoyl)-benzenesulphonyl chloride

The reaction is carried out in the same way as in Example 1.

$C_{13}H_6Cl_4O_3S$ (384.06); yield: 60%; m.p. 118° C.

EXAMPLE 11

Preparation of 3-benzoyl-4-chlorobenzenesulphonyl chloride a) Preparation of 2-chloro-5-nitrobenzophenone The reaction is carried out as in Example 10 a) by reacting benzene with 2-chloro-5-nitrobenzoyl chloride in the presence of aluminium chloride.

$C_{13}H_8ClNO_3$ (261.66; yield: 55%; m.p. 85° C.

b) Preparation of 5-amino-2-chlorobenzophenone

The reaction is carried out as in Example 10 b) starting with 2-chloro-5-nitrobenzophenone.

c) Preparation of 3-benzoyl-4-chlorobenzenesulphonyl chloride

The reaction is carried out in the same way as in Example 1.
$C_{13}H_8Cl_2O_3S$ (315.14); yield 40%; m.p. 92° C.

EXAMPLE 12

Preparation of 3-(4-chlorobenzoyl)-4l-chlorobenzenesulphonyl chloride a) Preparation of 2,4-dichloro-5-nitrobenzophenone The reaction is carried out as in Example 10 a) by reacting chlorobenzene with 2-chloro-5-nitrobenzoyl chloride in the presence of aluminium chloride.
$C_{13}H_7Cl_2NO_3$ (296.11); yield: 76%; m.p. 92° C.

b) Preparation of 5-amino-2,4'-dichlorobenzophenone

The reaction is carried out as in Example 10 b) starting with 2,4'-dichloro-5-nitrobenzophenone.

c) Preparation of 3-(4-chlorobenzoyl)-4-chlorobenzenesulphonyl chloride

The reaction is carried out as in Example 1.
$C_{13}H_7Cl_3O_3S$ (349.62); yield: 65%; m.p. 110° C.

EXAMPLE 13

Preparation of 4-benzoyl-3-chlorobenzenesulphonyl chloride

The reaction is carried out as in Example 10 a)

a) Preparation of 2-chloro-4-nitrobenzophenone by reacting benzene with 2-chloro-4-nitrobenzoyl chloride in the presence of aluminium chloride.

$C_{13}H_8ClNO_3$ (261.66); yield: 75%; m.p. 90° C.

b) Preparation of 4-amino-2-chlorobenzophenone

The reaction is carried out in the same way as in Example 10 b).

c) Preparation of 4-benzoyl-3-chlorobenzenesulphonyl chloride

The reaction is carried out in the same way as in Example 10 c).

EXAMPLE 14

Preparation of 4-chloro-3-(2-thenoyl)benzenesulphonyl chloride a) Preparation of 2-chloro-5-nitrophenyl-2-thienylketone The reaction is carried out as mentioned in Example 9 a) startng with 2-chloro-5-nitrobenzoyl chloride.
$C_{11}H_6ClNO_3S$ (267.69); yield: 85%; m.p. 105°–106° C.

b) Preparation of 5-amino-2-chlorophenyl-2-thienylketone hydrochloride

The reaction is carried out as mentioned in Example 9 b).
$C_{11}H_8ClNOS$, HCl (274.17); yield: 95%; m.p. 115°–120° C.

c) Preparation of 4-chloro-3-(2-thenoyl)benzenesulphonyl chloride

The reaction is carried out as mentioned in Example 1.

$C_{11}H_{16}Cl_2O_3S_2$ (321.20); yield: 72%; m.p. 84° C.

EXAMPLE 15

Preparation of 12-[3-(4-chlorophenylhydroxymethyl)-benzenesulphonamido]dodecanoic acid IC-1810

1.1 g of sodium borohydride are added in small portions to 4.8 g of 12-(3-benzoyl-4-chlorobenzenesulphonamido)dodecanoic acid in 200 ml of absolute ethanol, maintaining the temperature between 0° and 5° C. After stirring for 2 hours at ambient temperature, the reaction medium is neutralized by adding ethanolic hydrogen chloride and then evaporated to dryness under vacuum. The residue is taken up with ethyl acetate, the organic phase is washed with water, dried over sodium sulphate and then evaporated to dryness under vacuum. The product is obtained in the form of crystals (4g).

$C_{25}H_{34}ClNOS_5S$ (490.02); yield: 63%; m.p. 122° C.

The compounds IC-1796 and IC-1807 are prepared by this method.

EXAMPLE 16

11-(3-Benzyl-4-chlorobenzenesulphonamido)undecanoic acid IC-1808 a) Preparation of 3-benzyl-4-chloroaniline 6.8 g of lithium aluminium hydride, followed by 44.4 g of aluminium chloride and then 22 g of 5-amino-2-chlorobenzophenone dissolved in anhydrous ether are added in small amounts, under a nitrogen atmosphere, into 1000 ml of anhydrous ether which is cooled to 0° C. After stirring for 2 hours and under reflux, the excessive reagents are decomposed by very slowly adding 7 ml of 15% caustic soda and, finally, 21 ml of water. After filtering and washing the precipitate with 2×200 ml of ether, the organic phase is washed, dried over $Na_2SO_4$ and then evaporated to dryness under vacuum.

After purification on a silica column, eluting with a 3:2 hexane:$CH_3COOC_2H_5$ mixture, 17 g of the product are isolated in the form of a colourless lacquer.
$C_{13}H_{12}ClN$ (217.68); yield: 82%.

b) Preparation of 3-benzyl-4-chlorobenzenesulphonyl chloride

The reaction is carried out as mentioned in Example 1.
$C_{13}H_{10}Cl_2O_2S$ (301.19); yield: 52% c)
11-(3-benzyl-4-chlorobenzenesulphonamido)-dodecanoic acid

The reaction is carried out as mentioned in Example 6.

$C_{24}H_{32}ClNO_4S$ (467.04); yield: 30%; m.p. 88°–90° C.
The compound IC-1797 is prepared in the same way

Example 17

Preparation of 6-(2-benzoyl-4-chlorobenzenesulphonamido)-capronitrile 15 ml of redistilled triethylamine are added to 15.7 g of 4-chloro-2-benzoylbenzenesulphonyl chloride in 100 ml of anhydrous dichloromethane, and 5.6 g of 6-aminocapronitrile in 20 ml of dichloromethane are then added dropwise at 0° C.

After stirring overnight at 20° C., the reaction medium is evaporated to dryness under vacuum. The residue is taken up with 100 ml of water and extracted with 2×200 ml of ethyl acetate.

After drying, evaporating to dryness under vacuum and purification on a silica column ($CH_2Cl_2$), 19 g of a syrupy product are obtained.

$C_{19}H_{19}ClN_2S$ (390.89); yield: 95%.

EXAMPLE 18

Preparation of ethyl 11-(2-benzoyl-4-chlorobenzenesulphonamido)undecanoate IC-1740

7 ml of anhydrous triethylamine are added to 5.3 g of ethyl 11-aminoundecanoate hydrochloride in 30 ml of anhydrous methylene chloride and, after stirring for one hour at ambient temperature, 6.3 g of 2-benzoyl-4-chlorobenzenesulphonyl chloride are added dropwise. After stirring for 12 hours, the reaction medium is evaporated to dryness under vacuum, taken up with water and extracted with ethyl acetate. The organic phase which is washed with water until the washings are free of $Cl^-$ ions is dried over sodium sulphate and evaporated to dryness under vacuum.

By purification on a silica column, eluting with a 5:1 mixture of hexane:ethyl acetate, the pure product is obtained in the form of crystals.

$C_{26}H_{34}ClNO_5S$ (508.08); yield: 80%; m.p. 33°–34° C.
The compounds IC-1741 and 1742 are prepared in a similar way.

Example 19

Preparation of 11-[2-(2-chlorobenzoyl)-4-chlorobenzenesulphonamido]undecanamide a) Preparation of 11-[2-(2-chlorobenzoyl)-4-chlorobenzenesulphonamido]undecanoyl chloride.

19 g of redistilled thionyl chloride are added to 10.3 g of 11-[2-(2-chlorobenzoyl)-4-chlorobenzenesulphonamido]undecanoic acid in 130 ml of anhydrous benzene. After refluxing for 2 hours, the reaction medium is evaporated to dryness under vacuum and it gives a colourless oil which is used without further purification.

$C_{24}H_{28}Cl_3NO_4S$ (532.91); yield: 98% b) Preparation of 11-[2-(2-chlorobenzoyl)-4-chlorobenzenesulphonamido]undecanamide A solution of 2 g of 11-[2-(2-chlorobenzoyl)-4-chlorobenzenesulphonamido]undecanoic acid chloride in 15 ml of anhydrous benzene is saturated with ammonia at 10° C. After stirring for two hours, the reaction medium is evaporated to dryness under vacuum, the residue is taken up with water and then extracted with ethyl acetate. After evaporation, the organic phase gives crystals which are recrystallized in benzene (1.22 g).

$C_{24}H_{30}Cl_2N_2O_4S$ (513.48); yield: 70% m.p. 95°–97° C.

The compounds in Table I below were prepared according to the process described in Example 6.

TABLE I

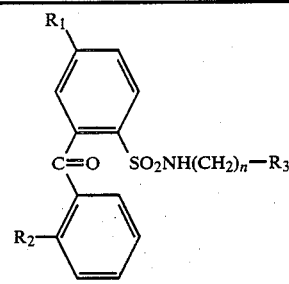

| Number of compounds | $R_1$ | $R_2$ | $R_3$ | n | Empirical formula | Molecular mass | Melting point | Yield |
|---|---|---|---|---|---|---|---|---|
| 1564 | $NO_2$ | H | COOH | 1 | $C_{15}H_{12}N_2O_7S$ | 364.34 | 120° | 67% |
| 1565 | Cl | H | COOH | 1 | $C_{15}H_{12}ClNO_5S$ | 353.78 | 125° | 59% |
| 1566 | $NO_2$ | H | COOH | 3 | $C_{17}H_{16}N_2O_7S$ | 393.39 | 162° | 66% |
| 1567 | Cl | H | COOH | 3 | $C_{17}H_{16}ClNO_5S$ | 381.84 | 148° | 60% |
| 1568 | $NO_2$ | H | COOH | 5 | $C_{19}H_{20}N_2O_7S$ | 420.45 | 100° | 65% |
| 1569 | Cl | H | COOH | 5 | $C_{19}H_{20}ClNO_5S$ | 409.90 | 94° | 78% |
| 1570 | Cl | Cl | COOH | 5 | $C_{19}H_{19}Cl_2NO_5S$ | 444.35 | 128° | 40% |
| 1571 | $NO_2$ | H | COOH | 10 | $C_{24}H_{30}N_2O_7S$ | 490.58 | 67° | 87% |
| 1572 | Cl | H | COOH | 10 | $C_{24}H_{30}ClNO_5S$ | 480.03 | 70° | 77% |
| 1573 | Cl | Cl | COOH | 3 | $C_{17}H_{15}Cl_2NO_5S$ | 416.279 | 112° | 27% |
| 1574 | Cl | Cl | COOH | 10 | $C_{24}H_{29}Cl_2NO_5S$ | 514.47 | 99° | 77% |
| 1575 | Cl | Cl | COOH | 1 | $C_{15}H_{11}Cl_2NO_5S$ | 388.22 | 166° | 55% |
| 1682 | H | H | COOH | 10 | $C_{24}H_{37}NO_5S$ | 445.58 | 70° | 65% |
| 1683 | H | H | COOH | 11 | $C_{25}H_{33}NO_5S$ | 459.61 | 80° | 65% |
| 1740 | Cl | H | $COOC_2H_5$ | 10 | $C_{26}H_{34}ClO_5S$ | 508.08 | 33–34 | 80% |
| 1741 | Cl | H | $COOC_2H_5$ | 5 | $C_{21}H_{24}ClO_5S$ | 437.94 | 55 | 55% |
| 1742 | Cl | H | $COOC_2H_5$ | 7 | $C_{23}H_{28}ClO_5S$ | 465.99 | 45 | 70% |

TABLE I-continued

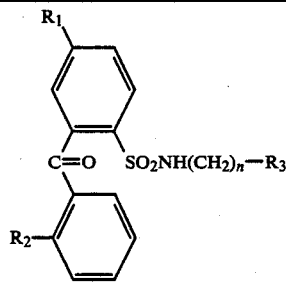

| Number of compounds | $R_1$ | $R_2$ | $R_3$ | n | Empirical formula | Molecular mass | Melting point | Yield |
|---|---|---|---|---|---|---|---|---|
| 1743 | Cl | Cl | COOH | 7 | $C_{21}H_{23}Cl_2O_5S$ | 472.38 | 76 | 60% |
| 1744 | Cl | H | COOH | 7 | $C_{21}H_{24}ClN_5S$ | 437.94 | 96 | 60% |
| 1745 | Cl | H | CN | 5 | $C_{19}H_{19}ClNO_3S$ | 390.89 | syrupy | 95% |
| 1755 | Cl | Cl | COOH | 11 | $C_{25}H_{31}Cl_2NO_5S$ | 528.50 | 76–78 | 58% |
| 1760 | Cl | Cl | $CONH_2$ | 10 | $C_{24}H_{30}Cl_2N_2O_4S$ | 513.48 | 95–97 | 65% |

Using the startng products (sulphochlorides and amino acids described above in the preparation of the compounds of the invention), the following products are obtained:

12-[4-chloro-2(4-chlorobenzoyl)benzenesulphonamido]dodecanoic acid,
11-[4-chloro-2-(4-chlorobenzoyl)benzenesulphonamido]undecanoic acid,
8-[4-chloro-2-(4-chlorobenzoyl)benzenesulphonamido]octanoic acid,
6-8  4-chloro-2-(4-chlorobenzoyl)benzenesulphonamido]hexanoic acid,
12-[4-chloro-2-(2,4-dichlorobenzoyl)benzenesulphonamido]dodecanoic acid,
11-[4-chloro-2-(2,4-dichlorobenzoyl)benzenesulphonamido]undecanoic acid,
8-]4-chloro-2-(2,4-dichlorobenzoyl)benzenesulphonamido]octanoic acid,
6-[4-chloro-2-(2,4-dichlorobenzoyl)benzenesulphonamido]hexanoic acid,
12-[2-(4-chlorobenzoyl)benzenesulphonamido]-dodecanoic acid,
11-[2(4-chlorobenzoyl)benzenesulphonamido]undecanoic acid,
8[2-(4-chlorobenzoyl)benzenesulphonamido]octanoic acid,
6-[2-(4-chlorobenzoyl)benzenesulphonamido]hexanoic acid,
12-[2-(2,4-dichlorobenzoyl)benzenesulphonamido]-dodecanoic acid,
11-[2-(2,4-dichlorobenzoyl)benzenesulphonamido]undecanoic acid,
8-2-(2,4-dichlorobenzoyl)benzenesulphonamido]octanoic acid,
6-2-(2,4-dichlorobenzoyl)benzenesulphonamido]hexanoic acid.

The compounds in Table II below were prepared according to the process described in Example 6.

TABLE II

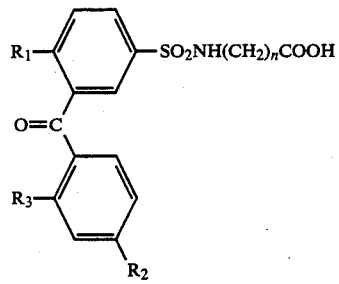

| Number of Compounds | $R_1$ | $R_2$ | $R_3$ | n | Empirical formula | Molecular mass | Melting point | Yield |
|---|---|---|---|---|---|---|---|---|
| 1684 | H | H | H | 10 | $C_{24}H_{31}NO_5S$ | 445.58 | 80° | 65% |
| 1685 | H | H | H | 11 | $C_{25}H_{33}NO_5S$ | 459.61 | 70°–75° | 65% |
| 1736 | Cl | H | H | 11 | $C_{25}H_{32}ClNO_5S$ | 494.05 | 75° | 41% |
| 1737 | Cl | H | H | 10 | $C_{24}H_{30}ClNO_5S$ | 480.03 | 79°–80° | 43% |
| 1761 | Cl | Cl | H | 10 | $C_{24}H_{29}Cl_2NO_5S$ | 514.47 | 80° | 60% |
| 1762 | Cl | Cl | H | 11 | $C_{25}H_{31}Cl_2NO_5S$ | 528.49 | 93° | 67% |
| 1763 | Cl | Cl | Cl | 10 | $C_{24}H_{28}Cl_3NO_5S$ | 548.91 | 94° | 38% |
| 1764 | Cl | Cl | Cl | 11 | $C_{25}H_{30}Cl_3NO_5S$ | 562.94 | 88° | 62% |

Using the starting products (sulphochlorides and amino acids described above in the preparation of the compounds of the invention), the following products are obtained:

12-(3-benzoyl-4-chlorobenzenesulphonamido)-dodecanoic acid, 11-(3-benzoyl-4-chlorobenzenesulphonamido)undecanoic acid,
8-3-benzoyl-4-chlorobenzenesulphonamido)octanoic acid,
6(3-benzoyl-4-chlorobenzenesulphonamido)hexanoic acid,
12-[3-(2,4-dichlorobenzoyl)benzenesulphonamido]-dodecanoic acid,
11-[3-(2,4-dichlorobenzoyl)benzenesulphonamido]undecanoic acid,
8-[3-(2,4-dichlorobenzoyl)benzenesulphonamido]octanoic acid,
6-[3-(2,4-dichlorobenzoyl)benzenesulphonamido]hexanoic acid,
12-[3-(4-chlorobenzoyl)benzenesulphonamido]-dodecanoic acid,
11-[3-(4-chlorobenzoyl)benzenesulphonamido]undecanoic acid,
8-[3-(4-chlorobenzoyl)benzenesulphonamido]octanoic acid,
6-[3-(4-chlorobenzoyl)benzenesulphonamido]hexanoic acid,
12-(4-chloro-3-(2,4-dichlorobenzoyl)benzenesulphonamico]-undecanoic acid,
11-[4-chloro-3-(2,4-dichlorobenzoyl)benzenesulphonamido]-undecanoic acid,
8-[4-chloro-3-(2,4-dichlorobenzoyl)benzenesulphonamido]-octanoic acid,
6-[4-chloro-3-(2,4-dichlorobenzoyl)benzenesulphonamido]-hexanoic acid.

The compounds in Table III below were prepared according to the process described in Example 6.

Using the starting products (sulphochlorides and amino acids described in the preparation of the compounds of the invention), the following products are obtained:
12-(4-benzoyl-3-chlorophenylbenzenesulphonamido)-dodecanoic acid,
11-(4-benzoyl-3-chlorophenylbenzenesulphonamido)undecanoic acid,
8-(4-benzoyl-3-chlorophenylbenzenesulphonamido)octanoic acid,
6-(4-benzoyl-3-chlorophenylbenzenesulphonamido)-hexanoic acid,
12[-4-(8-chlorobenzoyl)benzenesulphonamido]-dodecanoic acid,
11[-4-(4-chlorobenzoyl)benzenesulphonamido]undecanoic acid,
8-[4-(4-chlorobenzoyl)benzenesulphonamido]octanoic acid,
6-[4-(4-chlorobenzoyl)benzenesulphonamido]hexanoic acid,
12-[4-(2,4-dichlorobenzoyl)benzenesulphonamido]doecanoic acid,
11-[4-(2,4-dichlorobenzoyl)benzenesulphonamido]undecanoic acid,
8-[4-(2,4-dichlorobenzoyl)benzenesulphonamido]octanoic acid,
6-[4-(2,4-dichlorobenzoyl)benzenesulphonamido]hexanoic acid,
12-4-chloro-4-(2,4-dichlorobenzoyl)benzenesulphonamido]-dodecanoic acid,
11-[4-chloro-4-(2,4-dichlorobenzoyl)benzenesulphonamido]-undecanoic acid,
8-[4-chloro-4-(2,4-dichorobenzoyl)benzenesulphonamido]-odanoic acid,
6-[4-chloro-4-(2,4-dichlorobenzoyl)benzenesulphonamido]-hexanoic acid, The compounds in Table IV below were prepared according to the process described in Example 7.

TABLE III

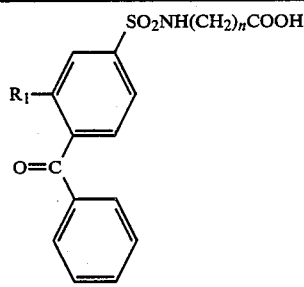

| Number of | $R_1$ | n | Empirical formula | Molecular mass | Melting point | Yield |
|---|---|---|---|---|---|---|
| 1686 | H | 10 | $C_{24}H_{31}NO_5S$ | 445.58 | 128° | 65% |
| 1687 | H | 11 | $C_{25}H_{33}NO_5S$ | 459.61 | 172° | 75% |
| 1739 | Cl | 11 | $C_{25}H_{32}ClNO_5S$ | 494.10 | 107° | 50% |

TABLE IV

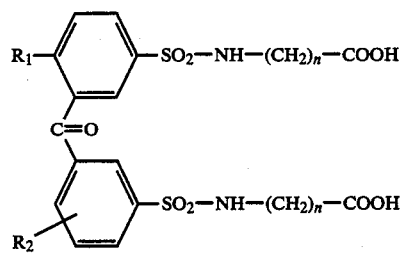

| Number of compounds | $R_1$ | $R_2$ | n | Empirical formula | Molecular mass | Melting point °C. | Yield % |
|---|---|---|---|---|---|---|---|
| 1688 | Cl | H | 10 | $C_{35}H_{51}ClN_2O_9S$ | 743.38 | 100–110 | 60 |
| 1689 | Cl | H | 11 | $C_{37}H_{55}ClN_2O_9S$ | 769.42 | 125 | 50 |

Using the starting products (sulphochlorides and amino acids described above in the preparation of the compounds of the invention), the following products are obtained:

8-{3-[3-(7-carboxyheptylsulphamoyl)benzoyl]-4-chlorobenzenesulphonamido}octanoic acid,
6-{3-[3-(5-carboxypentylsulphamoyl)benzoyl]-4-chlorobenzenesulphonamido}hexanoic acid,
12-{2-[3-(11-carboxyundecylsulphamoyl)benzoyl]-3-chlorobenzenesulphonamido}dodecanoic acid,
11-{2-[3-(10-carboxydecylsulphamoyl)benzoyl]-3-chlorobenzenesulphonamido}undecanoic acid,
8-{2-[3-(7-carboxyheptylsulphamoyl)benzoyl]-3-chlorobenzenesulphonamido}octanoic acid,
6-{2-[3-(5-carboxypentylsulphamoyl)benzoyl]-3-chlorobenzenesulphonamido}hexanoic acid,
12-{4-[3-(11-carboxyundecylsulphamoyl)benzoyl]-2-chlorobenzenesulphonamido}dodecanoic acid,
11-{4-[3-(10-carboxydecylsulphamoyl)benzoyl]-3-chlorobenzenesulphonamido}undecanoic acid,
8-{4-[3-(7-carboxyheptylsulphamoyl)benzoyl]-2-chlorobenzenesulphonamido}octanoic acid, and
6-{4-[3-(5-carboxypentylsulphamoyl)benzoyl]-2-chlorobenzenesulphonamido}hexanoic acid.

The compounds in Table V below were prepared according to the process described in Example 8.

TABLE V

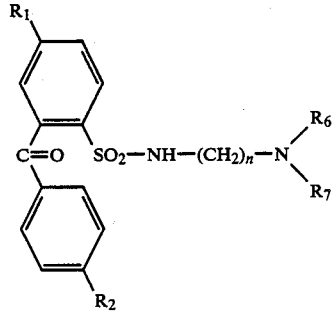

| Number of compounds | $R_1$ | $R_2$ | $N\begin{smallmatrix}R_6\\R_7\end{smallmatrix}$ | n | Empirical formula | Molecular mass | Melting point °C. | Yield % |
|---|---|---|---|---|---|---|---|---|
| 1340 | H | H | morpholino | 3 | $C_{20}H_{24}N_2O_4S$ | 388.49 | 121 | 65 |
| 1341 | H | H | morpholino | 2 | $C_{19}H_{22}N_2O_4S$ · HCl | 410.93 | 166 | 45 |
| 1342 | H | H | N(CH$_3$)$_2$ | 3 | $C_{18}H_{22}N_2O_3S$ | 382.92 | 153 | 45 |

TABLE V-continued $$\text{structure: } R_1\text{-phenyl-C(=O)-phenyl-}R_2 \text{ with } SO_2-NH-(CH_2)_n-NR_6R_7$$

| Number of compounds | R₁ | R₂ | N(R₆)(R₇) | n | Empirical formula | Molecular mass | Melting point °C. | Yield % |
|---|---|---|---|---|---|---|---|---|
| 1343 | Cl | H | morpholino | 2 | $C_{19}H_{21}ClN_2O_4S$ | 408.91 | 157 | 70 |
| 1344 | Cl | H | morpholino | 3 | $C_{20}H_{23}ClN_2O_4S$ | 422.94 | 116 | 80 |
| 1345 | Cl | H | N(CH₃)₂ | 3 | $C_{18}H_{21}ClN_2O_3S$ · $CH_3SO_3H$ | 477.01 | 164 | 25 |
| 1354 | NO₂ | H | morpholino | 2 | $C_{19}H_{21}N_3O_6S$ | 419.46 | 138 | 50 |
| 1360 | Cl | H | N(C₂H₅)₂ | 2 | $C_{19}H_{23}ClN_2O_3S$ | 431.89 | 125 | 45 |
| 1361 | NO₂ | H | morpholino | 3 | $C_{20}H_{23}N_3O_6S$ | 433.49 | 129 | 66 |
| 1362 | NO₂ | H | N(C₂H₅)₂ | 2 | $C_{18}H_{21}N_3O_5S$ | 391.45 | 200 | 30 |
| 1409 | H | Cl | N(CH₃)₂ | 3 | $C_{18}H_{21}ClN_2O_3S$ | 380.90 | 98 | 42 |
| 1410 | H | Cl | morpholino | 3 | $C_{20}H_{23}ClN_2O_4S$ | 422.94 | 130 | 55 |

The compounds in Tables VI and VIa below were prepared according to Example 9.

| 1738 | 3 | C$_{15}$H$_{15}$NO$_5$S$_2$ | 353.42 | 128–130 | 60 |

TABLE VIa

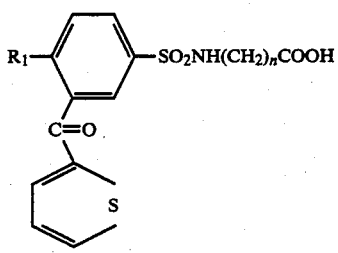

| Number of compounds | R$_1$ | n | Empirical formula | Molecular mass | Melting point °C. | Yield % |
|---|---|---|---|---|---|---|
| 1813 | Cl | 11 | C$_{23}$H$_{30}$ClNO$_5$S$_2$ | 500.08 | 74–75 | 73 |
| 1815 | Cl | 10 | C$_{22}$H$_{28}$ClNO$_5$S$_2$ | 486.05 | 62–63 | 66 |

The compounds in Table VII below are prepared according to Example 15.

TABLE VII

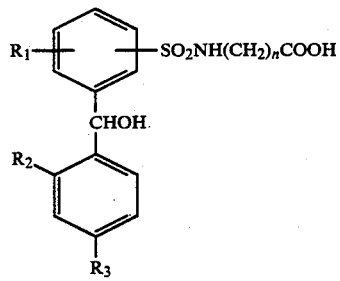

| Number of compounds | R$_1$ | R$_2$ | R$_3$ | n | Chained position | Empirical formula | Molecular mass | Melting point °C. | Yield % |
|---|---|---|---|---|---|---|---|---|---|
| 1796 | 5-Cl | Cl | H | 10 | 2- | C$_{24}$H$_{31}$Cl$_2$NO$_5$S | 516.48 | 125–130 | 66 |
| 1807 | 2-Cl | Cl | Cl | 11 | 5- | C$_{25}$H$_{32}$Cl$_3$NO$_5$S | 564.96 | 113.4 | 85 |
| 1810 | 2-Cl | H | H | 11 | 5- | C$_{25}$H$_{34}$ClNO$_5$S | 496.02 | 122 | 83 |

The compounds in Table VIIa below were prepared according to Example 9 and Example 15.

TABLE VIIa

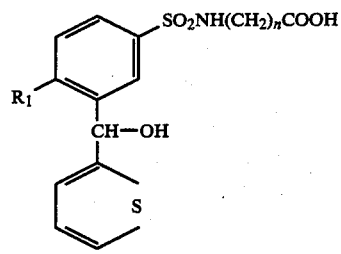

| Number of compounds | R$_1$ | n | Empirical formula | Molecular mass | Melting point °C. | Yield % |
|---|---|---|---|---|---|---|
| 1816 | Cl | 10 | C$_{22}$H$_{30}$ClNO$_5$S$_2$ | 488.07 | 109 | 50 |
| 1817 | Cl | 11 | C$_{23}$H$_{32}$ClNO$_5$S$_2$ | 502.10 | 117–118 | 59 |

The compounds in Table VIII below were prepared according to Example 16.

TABLE VIII

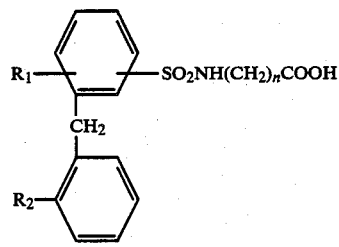

| Number of compounds | R$_1$ | R$_2$ | n | Chain postion | Empirical formula | Molecular mass | Melting point °C. | Yield % |
|---|---|---|---|---|---|---|---|---|
| 1797 | 5-Cl | Cl | 10 | 2- | C$_{24}$H$_{31}$Cl$_2$NO$_4$S | 500.49 | 77–80 | 49 |
| 1808 | 2-Cl | H | 10 | 5- | C$_{24}$H$_{32}$ClNO$_4$A | 467.04 | 88–90 | 30 |

The new compounds of the invention and their physiologically acceptable organic or inorganic salts have remarkable pharmacological properties.

Among the physiologically acceptable salts of the compounds of the invention, the following may be mentioned in particular:

as regards salts formed from an acid: alkali metal or alkaline earth metal salts or salts of an organic base, such as meglumate and aceglumate;

as regards salts formed from amines: hydrochlorides, sulphates, phosphates, methanesulphonates, tartrates, acetates, fumarates, succinates, pyruvates, phenoxyacetates, lactates, citrates and maleates.

The salts of the medicinal products according to the invention are:

1. Either those formed from a salification of the carboxyl group -COOH in compounds of the following formula:

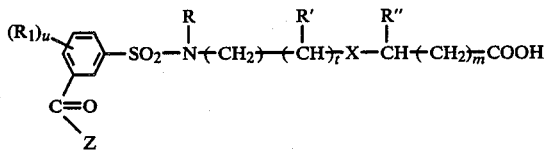

2. Or the salts formed from a salification with a strong base (NaOH or KOH) of the —NH and —COOH groups in compounds of the following formula:

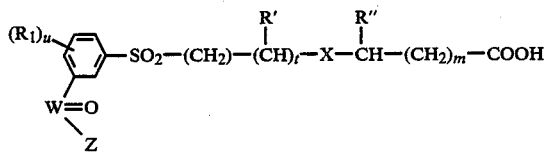

3. Or the salts of the compounds obtained by the salification of the substituent amino group of the aromatic ring in compounds of the following formula:

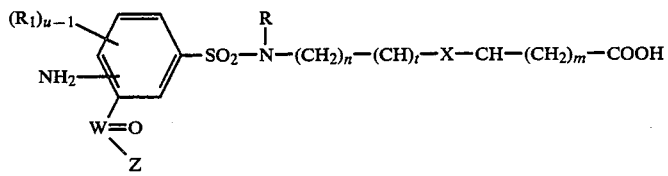

4. Or the salts of the compounds obtained by the salification of Y, when Y represents $NH_2$, $NHR_6$ or $NR_6R_7$.

In the first case, the unsalified compound is converted into the salt by reacting together, in a manner known per se, the base and product of the invention, in equimolecular quantities.

In the second case, the unsalified compound is converted into the salt by reacting together, in a manner known per se, two moles of the base and one mole of the product of the invention, in equimolecular quantities.

In the third case and the fourth case, the unsalified compound is converted into the salt by reacting together, in a manner known per se, the acid and the product of the invention, in equimolecular quantities.

The compounds according to the invention exert an anti-inflammatory and analgesic effect. Some of them strongly and selectively block the biosynthesis of the leukoytrienes $B_4$ (at the level of the polymorphonuclear leukocytes) involved in inflammatory processes, and the leukotrienes $C_4$ involved in allergic reactions such as asthma and certain types of allergic diseases.

The compounds according to the invention are also distinguished by the fact that they are devoid of toxicity at the active doses.

Their therapeutic index is compatible with their use as a medicinal product.

By way of example, various experiments for demonstrating the pharmacological properties and the good tolerability of the compounds according to the invention are reported below.

I - Anti-inflammatory activity

1) Kaolin-induced arthritis test 1.1 First experiment:

The invention of 0.05 ml of a sterile 10% strength suspension of kaolin into the metatarsal flexor sheath of the hind foot of a rat initially induces an oedematous reaction. An inflammatory arthritis then forms.

The early oedematous reaction appears from the first hour, and reaches its maximum between the fourth hour and the sixth hour. This is the manifestation of interest. The assessment of the volume of the foot enables the action of substances on the oedematous reaction to be studied. The measurements are carried out using a Giono and Chevilard plethysmometer.

The test products are administered orally (stomach tube) one hour before the injection of the kaolin.

The results are expressed as a percentage decrease in the inflammation in the treated animals compared with a control series of animals.

The batches are of 10 animals per dose and 10 control animals.

The results are also compared with series of animals treated with a reference product, ketoprofen.

The results relating to the compounds of the invention are collated in Table IX below.

The figures shown represent the mean of 10 animals.

TABLE IX

|  | 25 mg/kg | 50 mg/kg | 100 mg/kg |
|---|---|---|---|
| Ketoprofen | −30% | −51% | −73% |
| 1573 | −15% | −30% | −52% |
| 1570 | −10% | −25% | −52% |
| 1572 | −17% | −26% | −50% |
| 1565 | −15% | −20% | −45% |
| 1568 | −15% | −18% | −40% |
| 1575 | −18% | −21% | −37% |
| 1569 | −28% | −30% | −45% |
| 1567 | −12% | −15% | −20% |
| 1410 | −18% | −32% | −57% |
| 1361 | −25% | −30% | −48% |
| 1340 | −10% | −25% | −45% |
| 1344 | −10% | −15% | −18% |
| 1343 | — | — | — |
| 1571 | −17% | −26% | −50% |
| 1682 | −35% | −35% | −40% |
| 1683 | −25% | −30% | −40% |
| 1684 | −28% | −42% | −45% |
| 1686 | −50% | −50% | −50% |
| 1687 | −23% | −28% | −50% |
| 1688 | −25% | −28% | −48% |

The results show that, at a dose of 100 mg/kg, the majority of the compounds tested show a very distinct anti-inflammatory activity while showing the advantage, compared with ketoprofen, of not giving rise to adverse side effects, as a consequence of the absence of an effect on the biosynthesis of prostaglandins.

1.2 Second experiment:

In a second experiment, a more elaborate study was performed in order to ascertain the effect of the products, on the one hand on the acute phase of the inflammatory reaction (measured by the volume of the foot at the 8th hour), and on the other hand on the chronic phase (activity measured by the weight of the foot at the 12th hour).

As in the previous experiment, ketoprofen was used as the comparative product:

Results for the Acute Phase

The results are expressed as a percentage significant decrease in the volume of the treated foot compared with the controls. They are recorded in Table IXa below:

TABLE IXA

| PRODUCT | DOSE TESTED | | | 50% ACTIVE DOSE |
|---|---|---|---|---|
| | 25 mg/kg | 50 mg/kg | 100 mg/kg | |
| 1574 | −60 ± 6 | −65 ± 6 | −68 ± 5 | 25 mg/kg |
| Ketoprofen | −60 ± 5 | −68 ± 5 | −68 ± 5 | |
| 1736 | −45 ± 5 | −50 ± 5 | −55 ± 5 | 50 mg/kg |
| Ketoprofen | −47 ± 6 | −48 ± 5 | −55 ± 5 | |
| 1755 | −48 ± 5 | −50 ± 5 | −55 ± 5 | 25 mg/kg |
| Ketoprofen | −45 ± 6 | −48 ± 2 | −50 ± 5 | |
| 1761 | −38 ± 5 | −45 ± 5 | −50 ± 5 | 100 mg/kg |
| Ketoprofen | −40 ± 5 | −48 ± 5 | −60 ± 5 | |
| 1763 | −35 ± 5 | −45 ± 5 | −50 ± 5 | 100 mg/kg |
| Ketoprofen | −37 ± 5 | −48 ± 6 | −52 ± 3 | |
| 1764 | −45 ± 5 | −55 ± 5 | −60 ± 5 | 50 mg/kg |
| Ketoprofen | −47 ± 6 | −53 ± 3 | −58 ± 4 | |
| 1796 | −50 ± 5 | −55 ± 5 | −60 ± 5 | 25 mg/kg |
| Ketoprofen | −48 ± 5 | −55 ± 5 | −58 ± 5 | |
| 1797 | −50 ± 5 | −55 ± 5 | −60 ± 5 | 25 mg/kg |
| Ketoprofen | −30 ± 5 | −55 ± 5 | −58 ± 5 | |

Results for the Chronic Phase

The results are expressed as a percentage significant decrease in the weight of the treated foot compared with the controls, and are recorded in TABLE IXb below:

TABLE IXb

| PRODUCT | DOSE TESTED | | | 50% ACTIVE DOSE |
|---|---|---|---|---|
| | 25 mg/kg | 50 mg/kg | 100 mg/kg | |
| 1574 | −58 ± 5 | −60 ± 5 | −60 ± 5 | 25 mg/kg |
| Ketoprofen | −58 ± 5 | −65 ± 5 | −65 ± 5 | |
| 1736 | −45 ± 5 | −55 ± 5 | −58 ± 5 | 50 mg/kg |
| Ketoprofen | −48 ± 5 | −55 ± 5 | −60 ± 5 | |
| 1755 | −45 | −55 | −58 | 25 mg/kg |
| Ketoprofen | −44 ± 5 | −52 ± 6 | −55 ± 5 | |
| 1761 | −40 ± 5 | −45 ± 5 | −50 ± 5 | 100 mg/kg |
| Ketoprofen | −45 ± 5 | −50 ± 6 | −55 ± 7 | |
| 1763 | −38 ± 5 | −40 ± 5 | −48 ± 5 | 100 mg/kg |
| Ketoprofen | −45 ± 5 | −48 ± 5 | −55 ± 5 | |
| 1764 | −45 ± 5 | −52 ± 5 | −58 ± 5 | 50 mg/kg |
| Ketoprofen | −47 ± 5 | −51 ± 5 | −57 ± 5 | |
| 1796 | −50 ± 5 | −52 ± 5 | −58 ± 5 | 25 mg/kg |
| Ketoprofen | −50 ± 5 | −52 ± 5 | −55 ± 5 | |
| 1797 | −50 ± 5 | −58 ± 5 | −60 ± 5 | 25 mg/kg |
| Ketoprofen | −50 ± 5 | −55 ± 5 | −56 ± 5 | |

2) Carragheenin-Induced Oedema Test

In this test, 10 rats are used per test compound of the invention. Control batches of 10 rats also receive either the comparative compound (ketoprofen) or exclusively an NaCl solution.

An injection of carragheenin into the base of the hind foot of a rat induces an oedema, the volume of which is measured with a Lence plethysmometer (technique similar to that of C.A. Winter, E.A. Risley and G.W. Nuss, Proc. Soc. Exp. Biol. Med. 1962, 111, 544 and P. Lence, Arch. Inv. Pharmacodyn. 1962, 136, 237).

The compounds of the invention are administered orally (stomach tube) one hour before the injection of carragheenin.

The carragheenin is suspended at a concentration of 1% in a 0.9% isotonic sodium chloride solution. The volume injected into the rat's foot is 0.20 ml.

The volume of the foot is measured before the injection and 3 hours later. The antagonistic effect of the products towards carragheenin is reflected in the inhibition of the volume of the oedema compared with control rats. The latter receive only isotonic NaCl solution under identical conditions.

The results are expressed as a percentage inhibition of the inflammation compared with the control rats (mean of 10 animals).

2.1 First experiment:
The results are collated in Table X below:

TABLE X

| | 25 mg/kg | 50 mg/kg | 100 mg/kg |
|---|---|---|---|
| Ketoprofen | −25% | −45% | −65% |
| 1573 | −17% | −28% | −50% |
| 1570 | −20% | −29% | −40% |
| 1572 | −18% | −25% | −49% |
| 1565 | −18% | −22% | −49% |
| 1568 | −15% | −20% | −35% |
| 1575 | −15% | −18% | −35% |
| 1569 | −30% | −35% | −50% |
| 1567 | −8% | −10% | −10% |
| 1410 | −15% | −25% | −48% |
| 1361 | −15% | −25% | −45% |
| 1340 | −5% | −5% | −10% |
| 1344 | — | — | — |
| 1343 | −7% | −8% | −8% |
| 1571 | −23% | −27% | −48% |
| 1682 | −33% | −42% | −45% |
| 1683 | −25% | −30% | −35% |
| 1684 | −30% | −45% | −55% |
| 1686 | −50% | −50% | −55% |
| 1687 | −25% | −30% | −48% |
| 1688 | −25% | −32% | −50% |

2.2 Second experiment:
The results are collated in Table Xa below:

TABLE Xa

| PRODUCT | DOSE | | |
|---|---|---|---|
| | 25 mg/kg | 50 mg/kg | 100 mg/kg |
| 1574 | −40% ± 5 | −43% ± 5 | −45% ± 5 |
| Ketoprofen | −45% ± 5 | −50% ± 5 | −50% ± 5 |
| 1736 | −45% ± 5 | −48% ± 5 | −55% ± 5 |
| Ketoprofen | −48% ± 6 | −50% ± 3 | −60% ± 5 |
| 1755 | −45% ± 5 | −52% ± 5 | −55% ± 5 |
| Ketoprofen | −44% ± 5 | −55% ± 6 | −58% ± 6 |
| 1761 | −30% ± 5 | −35% ± 5 | −45% ± 5 |
| Ketoprofen | −35% ± 2 | −40% ± 5 | −55% ± 5 |
| 1763 | −30% ± 5 | −35% ± 5 | −45% ± 5 |
| Ketoprofen | −35% ± 5 | −45% ± 6 | −55% ± 3 |
| 1764 | −45% ± 5 | −48% ± 5 | −52% ± 5 |
| Ketoprofen | −47% ± 5 | −49% ± 7 | −50% ± 5 |
| 1796 | −45% | −48% | −55% |
| Ketoprofen | −50% ± 5 | −50% ± 5 | −55% ± 5 |
| 1797 | −45% ± 5 | −48% ± 5 | −55% ± 5 |
| Ketoprofen | −45% ± 5 | −50% ± 5 | −55% ± 5 |

3) Test of experimental granuloma induced by foreign body.

3.1 First experiment
Study of the following compounds:
1573, 1570, 1572, 1341, 1361, 1410.

This test consists in studying the subacute cellular phase which is developed in the 8 days which follow the implantation of a foreign body, a sponge of non-resorbable plastic, in the dorsal subcutaneous connective tissue in rats.

The granulomas formed are removed 8 days after the implantation; a histological study is carried out after fixing the tissue and staining sections with hematein/eosin. The observation is more especially concerned with the cell population of the primary phase of the formation of the granulation tissue: the reticulohistocytic cells, lymphocytes and more especially the macrophages.

The animals used are Wistar rats weighing 120–140 g and of the same origin, maintained under the same conditions of housing throughout the treatment (8 days).

The compounds of the invention are administered orally, in a gum suspension, in the morning in a fasted state, using an oesophageal tube.

After 8 days of treatment, the rats are sacrificed by decapitation and the granulomas removed and prepared for the purpose of histological examination.

The experiment conditions are as follows:
The animals are distributed in batches of 10;
Each test product is administered at 2 doses, of 50 and 100 mg, respectively, to 2 batches of 10 animals;
Ketoprofen is used by way of reference product at the same 2 doses and under the same conditions; and
A batch of 10 control animals receives no treatment.
The results are shown in Table XI below.

TABLE XI

| Compound No. | |
|---|---|
| 1573 | At both doses, the activity is very distinct, the connective tissue is of low density and does not show the characteristics of an inflammatory tissue. |
| 1570 | The anti-inflammatory activity is exhibited at the dose of 50 mg/kg and is distinct for the dose of 100 mg/kg. |
| 1572 | The anti-inflammatory activity is exhibited at the dose of 50 mg/kg and is distinct for the dose of 100 mg/kg. |
| 1361 | The anti-inflammatory activity is exhibited at both doses without, however, inhibiting the formation of a connective tissue of the scar type. |
| 1410 | The inflammatory reaction is attenuated at both doses. The action manifests itself, in particular, by the absence of a congestive reaction of the granulation tissue. |
| 1341 | Inflammatory reaction distinctly attenuated at both doses. The results are superior to those of the compound 1410. |
| KETOPROFEN | At both doses, a very substantial decrease in the inflammatory reaction is observed. |
| CONTROL | Appearance very characteristic of a granuloma of the inflammatory type in the course of formation. |

In conclusion, all the products tested exhibited an anti-inflammatory activity which was reflected in a histological modification of the tissues compared with the untreated control animals.

3.2 Second experiment:
Studies of the following compounds:
1574 - 1736 - 1755 - 1761 - 1763 - 1764 - 1796 - 1797

In this experiment, on the one hand a histological study of the granulomas is performed by sampling on day 8 (results recorded in Table XIa), and on the other hand a study of the weight of the granulomas was performed 10 days after the implantation (results recorded in Table XIb).

TABLE XIa

| Compound number | |
|---|---|
| 1574 | At the three doses, very distinct rarefaction of the inflammatory connective tissue. Connective tissue slack, few fibroblasts. Between the fibres, presence of mobile cells of the connective tissue. Giant cells containing a foreign body very rare. |
| 1736 | Very distinct slowing in the formation of the granulation tissue. Thin peripheral shell. Rarefaction of the fibroblasts. Collagen fibres thin and scattered. Presence of lymphocytes and polymorphonuclear cells; few macrophages. |
| 1755 | Granuloma poorly developed. Thin collagen fibres, few fibroblasts. Normal vascularization. Presence of mobile cells of the connective tissue. Connective tissue of low density. |
| 1761 | Diminished production of inflammatory granulation tissue compared with the control. Peripheral shell of the granuloma composed of fibroblasts and thin collagen fibres. Presence of lymphocytes, macrophages and histiocytes. Under the peripheral shell, granulation tissue of low density, composed of scattered fibroblasts between which the presence of mobile cells of the connective tissue is observed. Tissue well vascularized. |
| 1763 | Peripheral shell of low density, composed of fibroblasts and of collagen fibres of low density scattered between the fibroblasts and the fibres. Presence of mobile cells of the connective tissue: polymorphonuclear cells, lymphocytes and histiocytes, rare giant cells containing a foreign body, attached to the sponge fragments. |
| 1764 | Peripheral shell of low density and low cell content. Presence of mobile cells of the connective tissue between the fibroblasts and the collagen fibres. Presence of lymphocytes, macrophages, histiocytes and rare giant cells containing a foreign body. Granulation tissue only lightly inflammatory. |
| 1796 | Presence of many mobile cells of the connective tissue between the fibroblasts and the (thin) collagen fibres. Presence of lymphocytes, macrophages and histiocytes. Peripheral shell of low density and low cell content. Rare giant cells containing a foreign body. Granulation tissue only slightly inflammatory. |
| 1797 | Granuloma poorly developed around the foreign body. Thin peripheral shell. Thin collagen fibres. Normal vascularization. Presence of mobile cells of the connective tissue. Under the peripheral shell, connective tissue only slightly inflammatory. |

TABLE XIb

| PRODUCT | DOSE | | |
|---|---|---|---|
| | 25 mg/kg | 50 mg/kg | 100 mg/kg |
| 1574 | −48% | −50% | −55% |
| Ketoprofen | −50% ± 5 | −55% ± 5 | −55% ± 5 |
| 1736 | −48% ± 5 | −52% ± 5 | −55% ± 5 |
| Ketoprofen | −46% ± 5 | −50% ± 5 | −55% ± 5 |
| 1755 | −45% ± 5 | −50% ± 5 | −55% ± 5 |
| Ketoprofen | −44% ± 5 | −50% ± 5 | −60% ± 5 |
| 1761 | −25% ± 5 | −30% ± 5 | −45% ± 5 |
| Ketoprofen | −30% ± 5 | −40% ± 6 | −55% ± 7 |
| 1763 | −15% ± 5 | −20% ± 5 | −45% ± 5 |
| Ketoprofen | −25% ± 5 | −25% ± 5 | −48% ± 6 |
| 1764 | −45% ± 5 | −50% ± 5 | −55% ± 5 |
| Ketoprofen | −48% ± 5 | −50% ± 5 | −57% ± 5 |
| 1796 | −50% | −55% | −60% |
| Ketoprofen | −50% ± 5 | −50% ± 5 | −58% ± 6 |
| 1797 | −50% + 5 | −55% ± 5 | −60% ± 5 |
| Ketoprofen | −50% ± 5 | −50% ± 5 | −55% ± 5 |

II - Analgesic Activity

Randall and Sellitto's Test (Arch. Int. Pharmacodyn. 1957, CXI, 409-419).

Inflammation increases the sensitivity to pain, in particular to pressure, and analgesics raise the threshold of the sensitivity.

The inflammation is obtained by injecting 0.1 ml of a 20% strength aqueous suspension of brewer's yeast under the plantar aponeurosis of one of the hind feet. The pain is induced by a force applied to the plantar surface and gradually increased by 16 g/second. The pain threshold is assessed in terms of the force necessary and sufficient to initiate a characteristic reaction of withdrawing the foot.

The sensitivity to pain of the inflamed foot reaches a plateau 4 hours after the injection of the brewer's yeast, and then remains stable until the 6th hour. The pain threshold of the inflamed foot in control rats weighing 140 g is reached for pressures of 50 to 60 g, whereas it is around 160 g for the intact foot.

The action of the substance administered orally to series of 10 rats is expressed in terms of the percentage increase in the mean pain threshold, compared with that measured in the rats of a control series of 10 animals which have not received a compound of the invention.

The test products are administered orally (stomach tube) one hour before the injection of brewer's yeast.

The comparative compound used is ketoprofen.

1. First experiment

The results are collated in Table XII below:

TABLE XII

|  | 25 mg/kg | 50 mg/kg | 100 mg/kg |
|---|---|---|---|
| Ketoprofen | +22% | +55% | +78% |
| 1573 | +20% | +35% | +60% |
| 1570 | +15% | +25% | +53% |
| 1572 | +18% | +30% | +55% |
| 1565 | +18% | +28% | +42% |
| 1568 | +18% | +25% | +48% |
| 1575 | +15% | +19% | +35% |
| 1569 | +10% | +15% | +25% |
| 1567 | +12% | +15% | +20% |
| 1410 | +19% | +37% | +58% |
| 1361 | +20% | +25% | +45% |
| 1340 | +10% | +20% | +49% |
| 1344 | +18% | +18% | +25% |
| 1343 | +10% | +12% | +12% |
| 1571 | +25% | +32% | +36% |
| 1682 | +12% | +15% | +20% |
| 1683 | +15% | +20% | +30% |
| 1684 | +35% | +45% | +50% |
| 1686 | +35% | +50% | +50% |
| 1687 | +25% | +35% | +50% |
| 1688 | +25% | +32% | +50% |

2. Second experiment

The results are collated in Table XIIa below:

| PRODUCT | DOSE 25 mg/kg | DOSE 50 mg/kg | DOSE 100 mg/kg | 50% active dose |
|---|---|---|---|---|
| 1574 | +45% ± 6 | +50% ± 5 | +50% ± 5 | 50 mg/kg |
| Ketoprofen | +50% ± 5 | +55% ± 5 | +58% ± 5 |  |
| 1736 | +52% | +58% | +60% | 25 mg/kg |
| Ketoprofen | +51% ± 6 | +55% ± 5 | +60% ± 5 |  |
| 1755 | +40% ± 5 | +50% ± 5 | +55% ± 5 |  |
| Ketoprofen | +38% ± 6 | +52% ± 5 | +55% ± 6 |  |
| 1761 | +40% ± 5 | +45% ± 5 | +50% ± 5 |  |
| Ketoprofen | +45% ± 2 | +48% ± 5 | +55% ± 5 |  |
| 1763 | +40% ± 5 | +42% ± 5 | +45% ± 5 |  |
| Ketoprofen | +42% ± 6 | +48% ± 7 | +55% ± 8 |  |
| 1764 | +50% ± 5 | +55% ± 5 | +58% ± 5 | 25 mg/kg |
| Ketoprofen | +50% ± 5 | +57% ± 5 | +60% ± 5 |  |
| 1796 | +50% ± 5 | +55% ± 5 | +58% ± 5 | 25 mg/kg |
| Ketoprofen | +49% ± 5 | +50% ± 5 | +55% ± 5 |  |
| 1797 | +50% ± 5 | +55% ± 5 | +58% ± 5 |  |
| Ketoprofen | +55% ± 5 | +55% ± 5 | +58% ± 5 |  |

III — Mechanism of biochemical action

Membrane phospholipids are metabolized by the action of phospholipase $A_2$ to arachidonic acid, the latter leading via the cyclooxygenase pathway to the biosynthesis of prostaglandins and thromboxanes, and via the lipoxygenase pathway to the biosynthesis of leukotrienes.

The products of the invention were tested, on the one hand, on the human platelet cyclooxygenase pathway using aggregating agents (thrombin or a sub-aggregating concentration of arachidonic acid). No modification (no anticyclooxygenase effect) is detected with the products of the invention.

Additional studies were carried out to investigate a possible activity of the products on thromboxane synthetase and on prostacyclin synthetase, a subsequent stage in the biosynthesis of prostaglandins.

In addition, the products of the invention were tested on the 5-lipoxygenase pathway using human polymorphonuclear leukocytes, and this showed that some of them were inhibitors of 5-lipoxygenase.

1) Study of the Specific Action Towards Thromboxane Synthetase:

1.1 Human platelet suspension system

The platelets are incubated with arachidonic acid (5 μg/ml) in the presence of increasing doses of test products ($10^{-6}$M to $5 \times 10^{-5}$M). Platelets stimulated by arachidonic acid (AA) manufacture a large amount of thromboxane $A_2$ ($TXA_2$), which can be measured radioimmunologically in the form of a stable metabolite $TXB_2$.

The assay of the amount of $TXB_2$ in the medium is performed after a 1- to 15- minute incubation at 37° C., the measurements being made in comparison with a control suspension which has not been incubated with the test products.

Results: These are expressed as $IC_{50}$, that is to say as the concentration of the test product which permits 50% inhibition of the production of $TXB_2$.

| Test Product | $IC_{50}$ μM |
|---|---|
| 1572 | 12 |
| 1574 | 8 |
| 1736 | 6.2 |
| 1796 | 7.8 |
| 1797 | 5 |
| 1813 | 11 |

The $IC_{50}$ values obtained show that the test products are strong inhibitors of $TXB_2$ production.

In addition, at the doses studied ($10^{-6}$M to $5 \times 10^{-5}$M), it was possible to observe a dose-response relationship for the test products with respect to the inhibition of $TXB_2$ production.

1.2 Renal preparation model

Human glomeruli synthesize both thromboxanes, via thromboxane synthetase, and prostaglandins, via prostacyclin synthetase. The experiment consists in stimulating glomerular cells with arachidonic acid (5 ug/ml) and in assaying radioimmunologically the amount of thromboxane $B_2$ ($TXB_2$) and prostacyclin ($PGI_2$) produced in the presence of increasing concentrations of test products ($10^{-6}$M to $5\times10^{-5}$M).

As for the previous model, the results are expressed as $IC_{50}$ in comparison with a control suspension.

| Test Products | $IC_{50}$ | |
|---|---|---|
| | $TXB_2$ | $PGI_2$ |
| 1572 | 7 | 100 |
| 1574 | 5 | 100 |
| 1736 | 2.6 | >50 |
| 1796 | 3.2 | 50 |
| 1797 | 4.4 | >50 |
| 1813 | 2 | >50 |

The $IC_{50}$ values obtained (<10 μM) show that the test products are strong inhibitors of $TXB_2$ production, whereas they are only weak inhibitors of $PGI_2$ production ($IC_{50} \geq 50$ μM), and that it is hence possible to obtain a specific activity towards $TXB_2$.

In addition, at the doses used ($10^{-6}$M to $5\times10^{-5}$M), a dose-response relationship is observed in respect of the inhibition of $TXB_2$.

2) Activity in respect of the biosynthesis of leukotrienes 2.1 First experiment

Polymorphonuclear leukocytes are isolated from human blood and used during the 6 hours following the withdrawal. The viability of the cells is checked by trypan blue exclusion.

$5\times10^6$ cells are incubated for 10 minutes at 37° C. in the presence of the test product dissolved in DMSO, and are stimulated with ionophore A 23187 (Galbiochem, 10 μM) in PBS buffer at pH 7.4, $Ca^{2+}$ and $Mg^{2+}=1$ μM.

100 ng of prostaglandin $B_2$ ($PGB_2$), dissolved in methanol, are added at the end of the reaction to act as an internal standard.

On centrifugation, the culture supernatant is withdrawn. The latter is retrieved under argon and stored at −80° C. until analysed by HPLC.

This analysis is carried out by injecting 250 μl onto a 5 μm ODS ultrasphere column (Beckmann), with a gradient of acetonitrile (20–80%) in water, at pH 7.4.

The amounts of the different products which absorb at 269 nm, i.e. leukotrienes $B_4$ ($LTB_4$), isomers of $LTB_4$ and oxidized metabolites of $LTB_4$, are estimated by comparison with the internal standard.

The test product is used at a concentration of 40 μM.

The results recorded in the table below show the activity of the compounds on:
1. $LTB_4$
2. the isomers of $LTB_4$
3. the oxidized metabolites of $LTB_4$.

They are expressed either as a percentage inhibition, or as a percentage increase in the production of $LTB_4$, isomers of $LTB_4$ and oxidized metabolites of $LTB_4$ (designated by +).

| Product | $LTB_4$ | Isomers | Oxidized metabolites |
|---|---|---|---|
| 1571 | 60% | 53% | 70% |
| 1572 | 84% | 100% | 90% |
| 1574 | 95% | 100% | 100 |
| 1682 | +30% | +30% | 40% |
| 1683 | +15% | +15% | 30% |
| 1684 | 20% | 35% | 60% |
| 1685 | 50% | 70% | 70% |
| 1686 | 0% | 5% | 25% |
| 1688 | +35% | −35% | 20% |
| 1689 | −30% | −30% | 20% |
| 1687 | +16% | 0 | −30% |

2.2 Second experiment

The experimental model is the same as that described in Section 2.1. Other products are tested by comparison with the compound of the invention no. 1574, used as a control.

| Test Product | Results — Percentage inhibition of $LTB_4$ formation |
|---|---|
| 1574 | 95 |
| 1734 | 70 |
| 1736 | 100 |
| 1737 | 95 |
| 1743 | 20 |
| 1738 | 20 |
| 1755 | 100 |
| 1761 | 100 |
| 1763 | 100 |
| 1764 | 100 |
| 1796 | 100 |
| 1797 | 100 |

The results show that, at a concentration of 40 μM, most of the test products very strongly inhibit a biosynthesis of $LTB_4$.

2.3 Third experiment

Human polymorphonuclear Leukocytes are stimulated by calcium ionophore A 23187 (Calbiochem, 5 μM), in the presence or absence of the test products.

After 15 minutes' incubation at 37° C., assay of the leukotrienes $C_4$ ($LTC_4$) is performed radioimmunologically.

The results are expressed as $IC_{50}$, the concentration producing 50% inhibition of the production of $LTC_4$, by comparison with a control suspension which has not been incubated in the presence of the test products.

| Test Product | Results $IC_{50}$ μM |
|---|---|
| 1574 | 3 |
| 1736 | 3 |
| 1796 | 1.7 |
| 1797 | 1 |
| 1813 | 1 |

The $IC_{50}$ values obtained show that the products strongly inhibit the production of $LTC_4$.

A dose-response relationship is also observed between the doses tested, $10^{-6}$ and $5\times10^{-5}$M, and the inhibition of the biosynthesis of $LTC_4$.

2.4 Fourth experiment

Human polymorphonuclear leukocytes suspended with arachidonic acid and stimulated by calcium ionophore produce leukotrienes $B_4$ ($LTB_4$).

The test consists in incubating fresh human leukocytes with arachidonic acid at a dose of 10 μg/ml to which a tracer dose of tritium-labelled arachidonic acid has been added. The leukocytes are stimulated with calcium ionophore A 23187 (Calbiochem, 5 μM) and the amount of 5-hydroxyeicosatetraenoic acid (5-HETE) and $LTB_4$ produced is then assayed by HPLC.

5-HETE is the metabolite produced from arachidonic acid by 5-lipoxygenase, and from which $LTB_4$ is produced by the action of an isomerase.

The results are expressed as an integration of the surface of the peak obtained in HPLC by comparison with that obtained with control leukocytes which have not been incubated with the test products.

The results in brackets are expressed as a percentage inhibition of the production of 5-HETE and $LTB_4$.

|  | Control leukocytes | Results | | | |
|---|---|---|---|---|---|
|  |  | 1736 | 1796 | 1797 | 1813 |
| LTB4 | 3.419 | Undetectable (100) | 152 (95.7) | Undetectable (100) | Undetectable (100) |
| 5-HETE | 3.690 | 384 (89.6) | 127 (96.6) | Undetectable (100) | 181 (95.1) |

The results show that the test products very strongly inhibit both the production of 5-HETE and that of $LTB_4$, and this shows that the inhibition takes place at the 5-lipoxygenase level.

IV—Toxicological Study

The approximate oral $LD_{50}$ of the following compounds was studied: 1361, 1489 and 1572 in rats and mice and 1341, 1573, 1574, 1361, 1495, 1579, 1489 and 1572 in mice.

The compounds were suspended in a 3% strength solution of gum arabic so as to supply, in a volume of 2 ml for the rats, the equivalent of 50, 100, 200, 400 and 800 mg/kg, and, in a volume of 1 ml for the mice, 100, 200, 400, 800 and 1,600 mg/kg and, for 1573 and 1579, 3,200 mg/kg.

Gavage was performed by means of a metal tube, on batches of 5 animals for each series.

The animals were observed daily for 14 days.

The approximate $LD_{50}$ values are shown in the following table.

TABLE XIII

| Oral $LD_{50}$ | |
|---|---|
| Male Wistar rats, 200–400 g Compound No. | Female Swiss CF mice, weight 20 g Compound No. |
| 1361 >800 mg/kg | 1341- 250 mg/kg |
| 1572 >800 mg/kg | 1573 >3,200 mg/kg |
| 1489 >800 mg/kg | 1574 >1,600 mg/kg |
|  | 1361 >1,600 mg/kg |
|  | 1572 >1,600 mg/kg |
|  | 1495 >1,600 mg/kg |
|  | 1579 >3,200 mg/kg |
|  | 1489 >1,600 mg/kg |

The test products proved to be well tolerated orally in rats and mice. Their $DL_{50}$ is higher than the known one of ketoprofen.

The compounds are advantageously introduced as active principle into medicinal products intended for the treatment of inflammatory states or of allergic states, in particular those of a cutaneous or asthmatic nature, or for the treatment of certain pathological cardiovascular conditions or renal insufficiency.

For this purpose, the compounds according to the invention are packaged with the traditional excipients and additives, in particular those used for preparing tablets, powders, gelatin capsules, ampoules for oral administration and injectable solutions.

The medicinal products of the invention can advantageously be administered orally, in particular in the form of tablets, gelatin capsules, powders, solutions, suspensions or syrup.

The medicinal products according to the invention can also be administered topically, such as a cream, lotion, ointment or gel.

The medicinal products according to the invention can also be administered parenterally, for example when the active substance is in salt form.

For this reason, they are presented in the form of sterile or sterilizable solutions which are injectable or suitable for this use, for the extemporaneous preparation of injectable solutions. These solutions can be presented in the form of aqueous physiological solutions, especially isotonic solutions of one of these compounds, for example isotonic glucose or saline solutions, these examples naturally not being limiting in nature in the definition of the physiologically acceptable products which can be used for forming the injectable isotonic solutions.

The medicinal products according to the invention can also be administered in the form of suppositories.

The doses to be administered will be approximately 10 to 500 mg of active substance per day.

In the pharmaceutical preparations intended for oral administration, the unit dose is composed of approximately 10 to approximately 500 mg, and preferably from approximately 25 to 250 mg, of active substance per unit dose. In the pharmaceutical presentations intended for parenteral administration, the injectable preparations contain approximately 10 to 100 mg of active substance per unit dose.

We claim:

1. A compound of the formula:

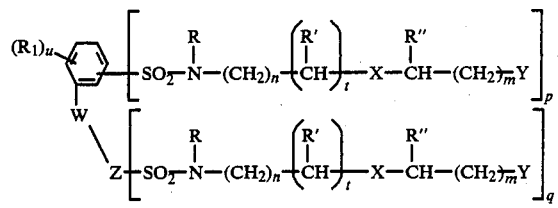

in which: W is =C=O, —CH₂— or =CHOH; Z is:

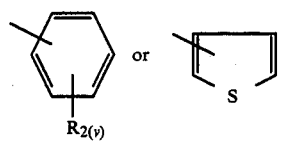

$R_1$ is Cl, F, Br, $NO_2$, $NH_2$, $CF_3$, alkyl of 1 to 4 carbon atoms, alkoxy of 1 to 4 carbon atoms, acetamido or benzamido;

$R_2$ is Cl, F, Br, $NO_2$, $NH_2$, $CF_3$, alkyl of 1 to 4 carbon atoms, alkoxy of 1 to 4 carbon atoms, acetamido or benzamido;

R is H, alkyl of 1 to 6 carbon atoms or benzyl;

R' and R" are individually H or alkyl of 1 to 4 carbon atoms; X is $-(CH_2)_r-$, $-CH=CH-$,

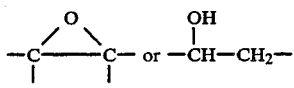

r is 0 or 1;

Y is $-COOR_3$,

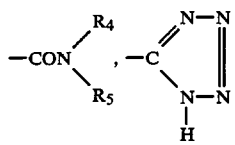

$-C\equiv N$, $-NH_2$, $-NHR_6$, $-NR_6R_7$ or

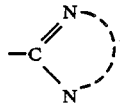

$R_3$ is H or alkyl of 1 to 4 carbon atoms;

$R_4$ and $R_5$ are individually H or alkyl of 1 to 4 carbon atoms;

$R_6$ and $R_7$ are individually alkyl of 1 to 4 carbon atoms, or together represent an alkylene group and form with the nitrogen atom a non-aromatic cyclic amine, or together represent a $-(CH_2)_2-O-(CH_2)_2-$ group and form with the nitrogen atom a morpholine group;

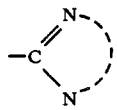

is a 5- or 6- membered nonaromatic ring in which the 2 or 3 atoms which form the remainder of the ring are selected from the group consisting of C, O and N;

provided that when Y is $-NH_2$, X is other than

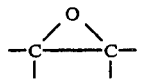

u is an integer of 0 to 2;
v is an integer of 0 to 2;
p is 0 or 1;
q is 0 or 1, p+q being at least 1;
n is an integer of 0 to 11;
m is an integer of 0 to 10;
t is 0 or 1; and
the total number of carbon atoms in each chain $-(CH_2)_n-(CH)_t-X-CH-(CH_2)_m-Y$ is from 2 to 20;

and the physiologically acceptable salts thereof.

2. The compound of claim 1, wherein W is $=C=O$.

3. The compound of claim 2, wherein Z is

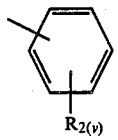

4. The compound of claim 3, wherein Y is $-COOR_3$.

5. The compound of claim 3, wherein Y is $-NH_2$, $-NHR_6$ or $-NR_6R_7$.

6. The compound of claim 3, wherein p or q is 0.

7. The compound of claim 6, wherein u+v is at least 1 and the total number of carbon atoms in each chain $-(CH_2)_n-(CH)_t-X-CH-(CH_2)_m-Y$ is at least 5.

8. The compound of claim 3, wherein p is 1, q is 1, u+v is at least 1 and the total number of carbon atoms in each chain $-(CH_2)_n-(CH)_t-X-CH-(CH_2)_m-Y$ is at least 5.

9. The compound of claim 1, wherein W is $=CH_2$.

10. The compound of claim 1, wherein W is $=CHOH$.

11. The compound of claim 1, wherein p is 1 and q is 0.

12. The compound of claim 11, wherein Y is $-COOR_3$.

13. The compound of claim 12, wherein W is $=C=O$.

14. The compound of claim 13, wherein the total number of carbon atoms in the chain $-(CH_2)_n-(CH)_t-X-CH-(CH_2)_m-Y$ is at least 5.

15. The compound of claim 12, wherein W is $=CH_2$.

16. The compound of claim 5, wherein the total number of carbon atoms in the chain $-(CH_2)_n-(CH)_t-X-CH-(CH_2)_m-Y$ is at least 5.

17. The compound of claim 12, wherein W is $=CHOH$.

18. The compound of claim 17, wherein the total number of carbon atoms in the chain $-(CH_2)_n-(CH)_t-X-CH-(CH_2)_m-Y$ is at least 5.

19. The compound of claim 12, wherein Z is

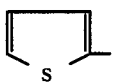

and the total number of carbon atoms in the chain

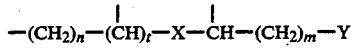

is at least 5

20. The compound of claim 11, having the formula:

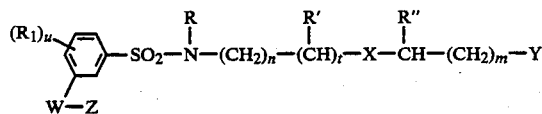

21. The compound of claim 20, wherein Y is —COOR$_3$.

22. The compound of claim 21, wherein W is >C=O.

23. The Compound of claim 22, wherein the total number of carbon atoms in the chain

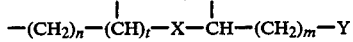

is at least 5.

24. The compound of claim 21, wherein W is >CH$_2$.

25. The compound of claim 24, wherein the total number of carbon atoms in the chain

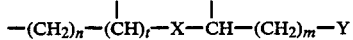

is at least 5.

26. The compound of claim 21, wherein W is >CHOH.

27. The compound of claim 26, wherein the total number of carbon atoms in the chain

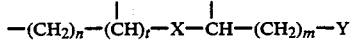

is at least 5.

28. The compound of claim 21, wherein Z is

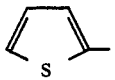

and the total number of carbon atoms in the chain

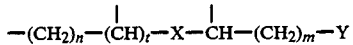

is at least 5.

29. The compound of claim 20, wherein W is >C=O and Z is

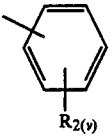

30. The compound of claim 29, wherein the total number of carbon atoms in the chain

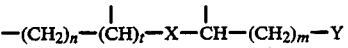

is at least 5.

31. The compound of claim 11, having the formula:

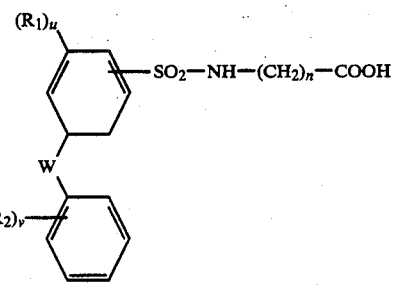

in which R$_1$ and R$_2$ are individually Cl, F or Br and n is an integer of 3 to 11.

32. The compound of claim 11, having the formula:

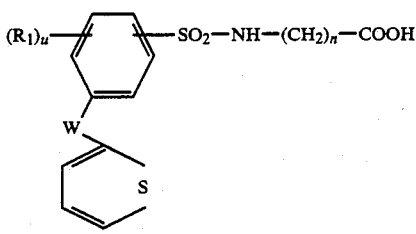

in which R$_1$ is Cl, F or Br and n is an integer of 3 to 11.

33. The compound of claim 11, wherein W is =C=O and Z is

34. The compound of claim 33, wherein the total number of carbon atoms in the chain.

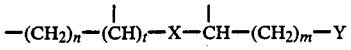

is at least 5.

35. The compound of claim 11, having the formula:

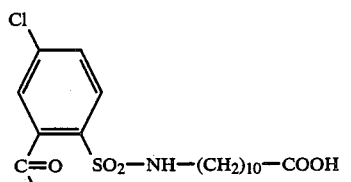
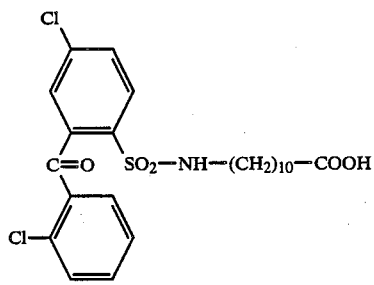
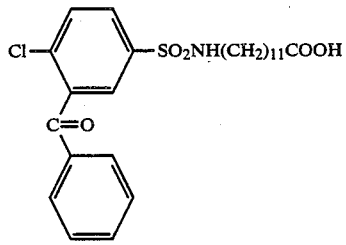
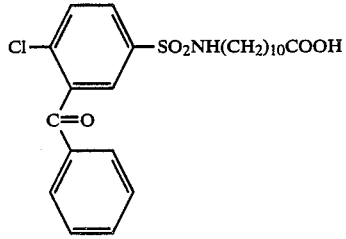
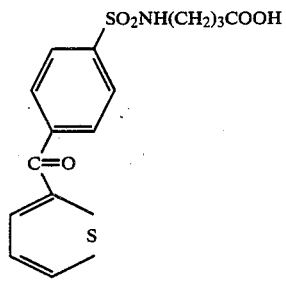
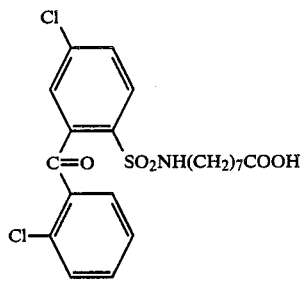
-continued
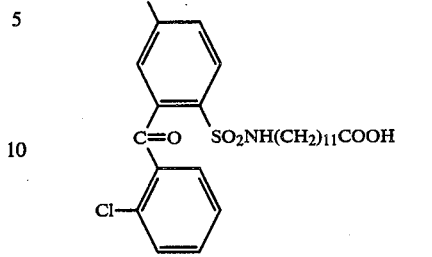
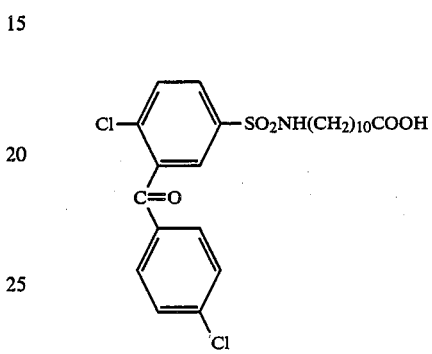
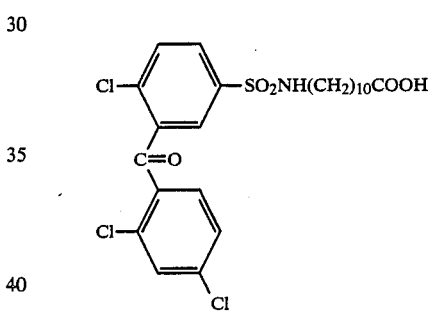
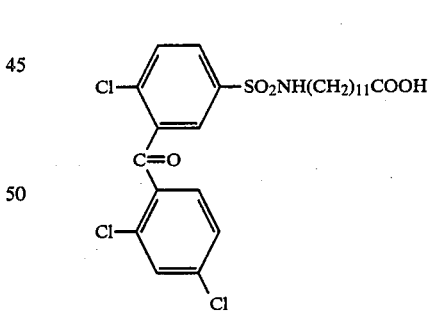
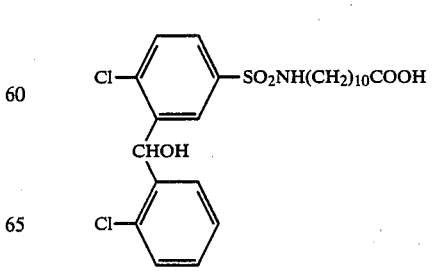

-continued

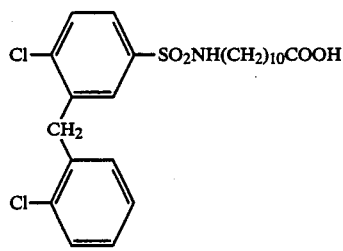

or

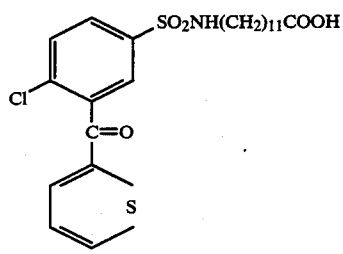

36. A pharmaceutical composition for inhibiting the biosynthesis of leukotrienes and for treating inflammatory, allergic or asthmatic conditions, comprising a compound of claim 1 and a pharmaceutically acceptable vehicle.

37. The composition of claim 36 constituting an injectable pharmaceutical composition; said compound of claim 1 comprising 10 to 100 mg per unit dose of said composition.

38. The composition of claim 36 constituting a pharmaceutical composition for oral administration; said compound of claim 1 comprising 10 to 500 mg per unit dose of said composition.

39. A pharmaceutical composition forinhibiting the biosynthesis of thromboxane synthetase and for treating a cardiovascular disorder or renal insufficiency, comprising a compound of claim 1 and a pharmaceutically acceptable vehicle.

40. The composition of claim 39 constituting an injectable pharmaceutical composition; said compound of claim 1 comprising 10 to 100 mg per unit dose of said composition.

41. The composition of claim 39 constituting a pharmaceutical composition for oral administration; said compound of claim 1 comprising 10 to 500 mg per unit dose of said composition.

42. A method for inhibiting a patient's biosynthesis of leukotrienes and/or thromboxane synthetase and for treating the patient for an inflammatory, allergic or asthmatic condition, a cardiovascular disorder or renal insufficiency, comprising the step of: administering a compound of claim 11 to the patient.

* * * * *